(12) United States Patent
Selwood et al.

(10) Patent No.: US 10,494,404 B2
(45) Date of Patent: Dec. 3, 2019

(54) QUINOLINIUM CONJUGATES OF CYCLOSPORIN

(71) Applicant: UCL BUSINESS PLC, London (GB)

(72) Inventors: David Selwood, Welwyn Garden (GB); David Baker, London (GB); Gyorgy Szabadkai, London (GB); Michael Roland Duchen, London (GB); Julia Marie Hill, Wembury (GB); Justin Neil Darrel Warne, Wallington (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 15/505,006

(22) PCT Filed: Aug. 19, 2015

(86) PCT No.: PCT/GB2015/052412
§ 371 (c)(1),
(2) Date: Feb. 17, 2017

(87) PCT Pub. No.: WO2016/027089
PCT Pub. Date: Feb. 25, 2016

(65) Prior Publication Data
US 2017/0349632 A1 Dec. 7, 2017

(30) Foreign Application Priority Data

Aug. 20, 2014 (GB) .................................. 1414806.8

(51) Int. Cl.
*C07K 7/64* (2006.01)
*A61K 47/54* (2017.01)
*G01N 33/94* (2006.01)

(52) U.S. Cl.
CPC ............ *C07K 7/645* (2013.01); *A61K 47/545* (2017.08); *G01N 33/94* (2013.01); *G01N 2800/28* (2013.01)

(58) Field of Classification Search
CPC ....... A61K 38/00; A61K 47/545; C07K 7/645
See application file for complete search history.

(56) References Cited

FOREIGN PATENT DOCUMENTS

| GB | 2472138 | 1/2011 |
|----|---------|--------|
| WO | WO 2003/033010 A | 4/2003 |
| WO | WO 2007/112352 A2 | 10/2007 |
| WO | WO 2008/139986 A1 | 11/2008 |
| WO | WO 2010/088573 A1 | 8/2010 |
| WO | WO 2011/010084 A2 | 1/2011 |
| WO | WO 2016/027089 A1 | 2/2016 |

OTHER PUBLICATIONS

Malouitre, et al., "Mitochondrial targeting of cyclosporin A enables selective inhibition of cycophilin-D and enhanced cytoprotection after glucose and oxygen deprivation," *Biochem J*, 425:137-148, (2010).
Shanmuganathan, et al., "Mitochondrial permeability transition pore as a target for cardioprotection in the human heart," *Am J Physiol Heart Circ Physiol*, 289:H237-H242, (2005).
Al-Izki, et al., "Practical guide to the induction of relapsing progressive experimental autoimmune encephalomyelitis in the Biozzi ABH mouse," Multiple Sclerosis and Related Disorders, 1:29-38, (2012).
Al-Izki, et al., "Lesional-targeting of neuroprotection to the inflammatory penumbra in experimental multiple sclerosis," *Brain: A Journal of Neurology*, 137:92-108, (2014).
Amor, et al., "Identification of epitopes of myelin oligodendrocyte glycoprotein for the induction of experimental allergic encephalomyelitis in SJL and Biozzi AB/H mice," *J Immunol*, 153:4349-4356, (1994).
Astin, et al., "No evidence for a local renin-angiotensin system in liver mitochondria," *Scientific Reports*, 3:2467, (2013).
Bainbridge, et al., "In vivo gene transfer to the mouse eye using an HIV-based lentiviral vector; efficient long-term transduction of corneal endothelium and retinal pigment epithelium," *Gene Therapy*, 8:1665-1668, (2001).
Baker, et al., "Critical appraisal of animal models of multiple sclerosis," *Mult Scler Journal*, 17(6):647-657, (2011).
Jackson, et al., "Cannabinoid-Receptor 1 Null Mice are Susceptible to Neurofilament Damage and Caspase 3 Activation," *Neuroscience*, 134:261-268 (2005).
Lim, et al., "Mitochondrial cyclophilin-D as a potential therapeutic target for post-myocardial infarction heart failure," *J Cell Mol Med*, 15(11):2443-2451, (2011).
McEwan, et al., "Truncation of TRIM5 in the *Feliformia* Explains the Absence of Retroviral Restriction in Cells of the Domestic Cat," *Journal of Virology*, 83(16):8270-8275, (2009).
Naldini, et al., "In Vivo Gene Delivery and Stable Transduction of Nondividing Cells by a Lentiviral Vector," *Science*, 272:263-267 (1996).
Nikolovska-Coleska, et al., "Development and optimization of a binding assay for the XIAP BIR3 domain using fluorescence polarization," *Anal Biochem*, 332:261-273, (2004).
Roehrl, et al., "A General Framework for Development and Data Analysis of Competitive High-Throughput Screens for Small-Molecule Inhibitors of Protein—Protein Interactions by Flourescence Polarization," *Biochemistry*, 43(51):16056-16066, (2004).
Schinkel, et al., "Absence of the mdr1a P-Glycoprotein in Mice Affects Tissue Distribution and Pharcokinetics of Dexamethasone, Digoxin, and Cyclosporin A," *J Clin Invest*, 96:1698-1705, (1995).
Ylinen, et al., "Conformational Adaption of Asian Macaque TRIMCyp Directs Lineage Specific Antiviral Activity," *PLoS Pathogens*, 6(8):e1001062, (2010).
Zufferey, et al., "Multiply attenuated lentiviral vector achieves efficient gene delivery in vivo," *Nature Biotech*, 15:871-875, (1997).
Giorgio, et al., "Dimers of mitochondrial ATP synthase form the permeability transition pore," *PNAS*, 110(15):5887-5892, (2013).

(Continued)

*Primary Examiner* — Kaipeen E Yang
(74) *Attorney, Agent, or Firm* — Alston & Bird, LLP

(57) ABSTRACT

The present invention relates to conjugates of cyclosporin with quinolium mitochondrial targeting groups, and their therapeutic uses.

10 Claims, 8 Drawing Sheets

(56) References Cited

OTHER PUBLICATIONS

Alavian, et al., "An uncoupling channel within the c-subunit ring of the $F_1F_0$ ATP synthase is the mitochondrial permeability transition pore," *PNAS*, 111(29):10580-10585, (2014).
Bonora, et al., "Role of the c subunit of the $F_0$ ATP synthase in mitochondrial permeability transition," *Cell Cycle*, 12(4):674-683, (2013).
Halestrap, et al., "The mitochondrial permeability transition: A current perspective on its identity and role in ischaemia/reperfusion injury," *Journal of Molecular and Cellular Cardiology*, 78:129-141, (2015).
Giorgio, et al., "Cyclophilin D Modulates Mitochondrial $F_0F_1$-ATP Synthase by Interacting with the Lateral Stalk of the Complex," *The Journal of Biological Chemistry*, 284(49):33982-33988, (2009).
Chinopoulos, et al., "Modulation of $F_0F_1$-ATP synthase activity by cyclophilin D regulates matrix adenine nucleotide levels," *The FEBS Journal*, 278:1112-1125, (2011).
Basso, et al., "Phosphate Is Essential for Inhibition of the Mitochondrial Permeability Transition Pore by Cyclosporin A and by Cyclosporin D Ablation," *The Journal of Biochemical Chemistry*, 283(39):26307-26311, (2008).
Campbell, et al., "The central role of mitochondria in axonal degeneration in multiple sclerosis," *Mult Scler Journal*, 20(14):1806-1813, (2014).
Barrientos, et al., "Axonal Degeneration Is Mediated by the Mitochondrial Permeability Transition Pore," *The Journal of Neuroscience*, 31(3):966-978, (2011).
Dutta, et al., "Mitochondrial Dysfunction as a Cause of Axonal Degeneration in Multiple Sclerosis Patients," *Ann Neurol*, 59:478-489, (2006).
Mahad, et al., "Mitochondrial defects in acute multiple sclerosis lesions," *Brain: A Journal of Neurology*, 131:1722-1735, (2008).
Kapoor, et al., "Blockers of Sodium and Calcium Entry Protect Axons from Nitric Oxide-Mediated Degeneration," *Ann Neurol*, 53:174-180, (2003).
Hazelton, et al., Cyclophilin D is predominantly expressed in mitochondria of GABAergic interneurons, *J Neurosci Res*, 87(5):1250-1259, (2009).
Forte, et al., "Cyclophilin D inactivation protects axons in experimental autoimmune encephalomyelitis, an animal model of multiple sclerosis," *PNAS*, 104(18):7558-7563, (2007).
Savino, et al., "The P66Shc/Mitochondrial Permeability Transition Pore Pathway Determines Neurodegeneration," *Oxidative Medicine and Cellular Longevity*, 2013:719407, (2013).
Mbye, et al., "Attenuation of acute mitochondrial dysfunction after traumatic brain injury in mice by NIM811, a non-immunosuppressive cyclosporine A analog," *Experimental Neurology*, 209:243-253, (2008).
Hånell, "Traumatic brain injury-induced axonal phenotypes react differently to treatment," *Acta Neuropathol*, 129:317-332, (2015).
Guo, et al., "Cyclophilin D Deficiency Rescues Axonal Mitochondrial Transport in Alzheimer's Neurons," *PLoS ONE*, 8(1):e54914, (2013).
Du, et al., "Cyclophilin D deficiency improves mitochondrial function and learning/memory in aging Alzheimer disease mouse model," *Neurobiology of Aging*, 32:398-406, (2011).
Martin, et al., "The mitochondrial permeability transition pore regulates Parkinson's disease development in mutant α-synuclein transgenic mice," *Neurobiology of Aging*, 35:1132-1152, (2014).
Quintanilla, et al., "Mitochondrial permeability transition pore induces mitochondria injury in Huntington disease," *Molecular Neurodegeneration*, 8:45, (2013).
Reddy, et al., "Abnormal mitochondrial dynamics and synaptic degeneration as early events in Alzheimer's disease: Implications to mitochondria-targeted antioxidant therapeutics," *Biochimica et Biophysica Acta*, 1822:639-649, (2012).
Readnower, et al., "Post-Injury Administration of the Mitochondrial Permeability Transition Pore Inhibitor, NIM811, Is Neuroprotective and Improves Cognition after Traumatic Brain Injury in Rats," *Journal of Neurotrama*, 28:1845-1853, (2011).

Nakagawa, et al., "Cyclophilin D-dependent mitochondrial permeability transition regulates some necrotic but not apoptic cell death," *Nature*, 434:652-658, (2005).
Baines, et al., "Loss of cyclophilin D reveals a critical role for mitochondrial permeability transition in cell death," *Nature*, 434:658-662, (2005).
Kato, et al., "The targeting of cyclophilin D by RNAi as a novel cardioprotective therapy: evidence from two-photon imaging," *Cardiovascular Research*, 83:335-344, (2009).
Wu, et al., "Blocking the mitochondrial permeability transition pore with cyclosporine-A can restore cardioprotection of ischemic postconditioning in hypercholesterolemic rat heart," *European Review for Medical and Pharmacological Sciences*, 19:446-454, (2015).
Barbarino, et al., "PharmGKB summary: cyclosporine and tacrolimus pathways," *Pharmacogenet Genomics*, 23(10):563-585, (2013).
Malouitre, et al., "Mitochondrial targeting of cyclosporine A enables selective inhibition of cyclophilin-D and enhanced cytoprotection after glucose and oxygen deprivation," *Biochem J*, 425:137-148, (2010).
Davis, et al., "Structural and Biochemical Characterization of the Human Cyclophilin Family of Peptidyl-Prolyl Isomerases," *PLoS Biol*, 8(7):e1000439, (2010).
Gogarten, et al., "A Case of Severe Cerebral Trauma in a Patient Under Chronic Treatment with Cyclosporine A," Journal of Neurosurgical Anesthesiology, 10(2):101-105, (1998).
The Multiple Sclerosis Study Group, "Efficacy and Toxicity of Cyclosporine in Chronic Progressive Multiple Sclerosis: A Randomized, Double-blinded, Placebo-controlled Clinical Trial," *Ann Neurol*, 27:591-605, (1990).
Porteous, et al., "P-glycoprotein (Mdr1a/1b) and breast cancer resistance protein (Bcrp) decrease the uptake of hydrophobic alkyl triphenylphosphonium cations by the brain," *Biochimica et Biophysica Acta*, 1830:3458-3465, (2013).
Dube, et al., "A mitochondrial-targeted cyclosporine A with high binding affinity for cyclophilin D yields improved cytoprotection of cardiomyocytes," *Biochem J*, 441:901-907, (2012).
Macarron, et al., "Yin and Yang in medicinal chemistry: what does drug-likeness mean?", *Future Med Chem*, 3(5):505-507, (2011).
Sharma, et al., "Relationship between lipophilicity of BCS class III and IV drugs and the functional activity of *peroral* absorption enhancers," *Il Farmaco*, 60:870-873, (2005).
Hogan, et al., "Transcriptional regulation by calcium, calcineurin, and NFAT," *Genes and Development*, 17:2205-2232, (2003).
Rasaiyaah, et al., "HIV-1 evades innate immune recognition through specific cofactor recruitment," *Nature*, 503:402-405, (2013).
Hoye, et al., "Targeting Mitochondria," *Accounts of Chemical Research*, 41(1):87-97, (2008).
Rodrigues, et al., "*Plasmodium berghei*: In vitro and in vivo activity of dequalinium," *Experimental Parasitology*, 115:19-24, (2007).
Smulik, et al., "Synthesis of Cyclosporin A-Derived Affinity Reagents by Olefin Metathesis," *Organic Letters*, 4(12):2051-2054, (2002).
Lemasters, et al., "Imaging of Mitochondrial Polarization and Depolarization with Cationic Fluorophores," *Methods in Cell Biology*, 80:283-295, (2007).
Chung, et al., "Potential role of the low-density lipoprotein receptor family as mediators of cellular drug uptake," *Advanced Drug Delivery Reviews*, 56:1315-1334, (2004).
Gallay, et al., "Profile of alisporivir and its potential in the treatment of hepatitis C," *Drug Design, Development and Therapy*, 7:105-115, (2013).
Su, et al., "Genetic inactivation of the p66 isoform of ShcA is neuroprotective in a murine model of multiple sclerosis," *European Journal of Neuroscience*, 35:562-571, (2012).
O'Neill, et al., "Therapy of chronic relapsing experimental allergic encephalomyelitis and the role of the blood-brain barrier: elucidation by the action of the Brequinar sodium," *Journal of Neuroimmunology*, 38:53-62, (1992).
Kappos, et al, "Cyclosporine Versus Azathioprine in the Long-Term Treatment of Multiple Sclerosis—Results of the German Multicenter Study," *Annal Neurol*, 23:56-63, (1988).
Su, et al., "Mitochondrial dysfunction and neurodegeneration in multiple sclerosis," *Frontiers in Physiology*, 4:169, (2013).

(56) References Cited

OTHER PUBLICATIONS

PCT International Search Report and Written Opinion of the International Search Authority for application PCT/GB2015/052412 dated Nov. 26, 2015.
PCT International Preliminary Report on Patentability for application PCT/GB2015/052412 dated Feb. 21, 2017.

QUINOLINIUM CONJUGATES OF CYCLOSPORIN

FIELD OF THE INVENTION

The present invention relates to conjugates of cyclosporin with quinolinium mitochondrial targeting groups, and their therapeutic uses.

BACKGROUND

Ischaemic diseases, notably myocardial infarction and stroke, are the leading cause of death and disability throughout the world. Following an ischaemic episode, early restoration of blood flow is essential to restrict tissue damage. However, when blood supply is restored to ischaemic cells, the newly returning blood can adversely affect the damaged tissue. This is known as reperfusion injury, and often causes further damage and cell death following an ischaemic episode. It is therefore a therapeutic goal to mitigate and avoid ischaemia/reperfusion (I/R) injury. There are currently no effective therapeutic treatments for ischaemia/reperfusion injury.

Cyclosporin A (CsA) is well known as an immunosuppressive drug. It has been proposed for use in treating ischaemia/reperfusion injury. However, experimental models and pilot trials to investigate the efficacy of cyclosporin in treating ischaemia/reperfusion yielded highly variable and only marginal effects. Further, administration of cyclosporin to patients can lead to adverse side effects, due to the toxicity of the compound. Subsequently, WO 2011/010084 described treatment of ischaemia/reperfusion injury by selective inhibition of mitochondrial cyclophilin D (CyP-D) using cyclosporin conjugated to mitochondrial targeting groups.

SUMMARY OF THE INVENTION

The present invention arises from the surprising finding that conjugates of cyclosporin to quinolinium mitochondrial targeting groups are associated with reduced toxicity as compared to unconjugated cyclosporin or cyclosporin conjugated to other mitochondrial targeting groups. Conjugates of cyclosporin to quinolinium are also potent inhibitors of cyclophilin D and demonstrate neuroprotective properties in an animal model of ischaemia/reperfusion injury. Conjugates of cyclosporin to quinolinium have also been found to demonstrate neuroprotective properties in animal models of neurodegenerative conditions. Conjugates of cyclosporin to quinolinium therefore represent promising candidates for a therapeutic approach to the treatment of neurodegenerative conditions and ischaemia/reperfusion injury.

Accordingly, the present invention provides a cyclosporin conjugate which is a compound of formula (I) or a pharmaceutically acceptable salt thereof:

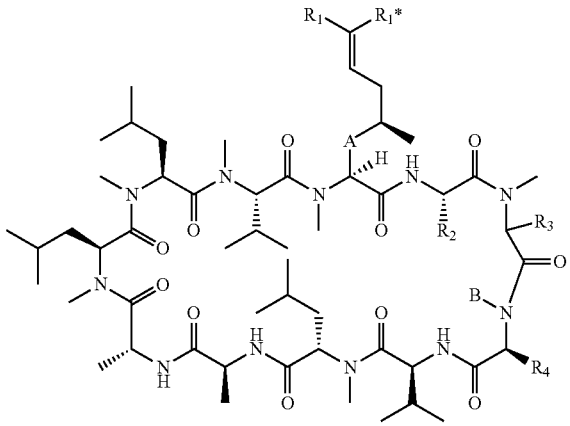

(I)

in which:
A represents

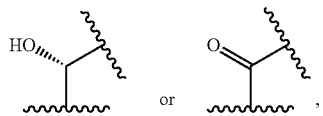

B represents methyl or ethyl
$R_2$ represents ethyl or isopropyl
$R_4$ represents —$CH_2CH(CH_3)CH_3$, —$CH_2CH(CH_3)CH_2CH_3$, —$CH(CH_3)CH_3$ or —$CH(CH_3)CH_2CH_3$,
either (a) one of $R_1$ and $R_1^*$ represents -$L_1Z_1$ and the other represents hydrogen, and $R_3$ represents hydrogen, $C_1$-$C_3$ alkyl or $C_2$-$C_4$ alkenyl, (b) one of $R_1$ and $R_1^*$ represents methyl and the other represents hydrogen, and $R_3$ represents -$L_3Z_3$, or (c) one of $R_1$ and $R_1^*$ represents -$L_1Z_1$ and the other represents hydrogen, and $R_3$ represents -$L_3Z_3$,
$L_1$ and $L_3$ independently represent a $C_1$-$C_6$ alkylene moiety, a $C_2$-$C_6$ alkenylene moiety or a —$(CH_2CH_2O)_n(CH_2)_m$— moiety in which n represents 1 to 3 and m represents 0 to 2, and
$Z_1$ and $Z_3$ independently represent a quinolinium ring which is unsubstituted or substituted by one or more substituents selected from a halogen atom, a $C_1$-$C_6$ alkyl group, a $C_1$-$C_6$ haloalkyl group, a —OR' group, a —COOR' group, a —CONR'R" group and a —NR'R" group, wherein R' and R" are the same or different and represent hydrogen or a $C_1$-$C_6$ alkyl group.

The present invention further provides a pharmaceutical composition comprising a conjugate of the invention and a pharmaceutically acceptable excipient, diluent or carrier.

The present invention further provides a conjugate of the invention for use in the treatment of the human or animal body.

The present invention further provides a conjugate of the invention for use in the treatment or prevention of a disease or disorder susceptible to amelioration by inhibition of cyclophilin D.

The present invention further provides use of a conjugate of the invention in the manufacture of a medicament for use in the treatment of a disease or disorder susceptible to amelioration by inhibition of cyclophilin D.

The present invention further provides a method of treating a patient suffering from or susceptible to disease or disorder susceptible to amelioration by inhibition of cyclophilin D, which method comprises administering to said patient a conjugate of the invention.

The present invention further provides a non-therapeutic use of a conjugate of the invention as a reagent for an experimental assay.

DESCRIPTION OF THE FIGURES

FIG. 1 depicts the mean daily clinical score after induction of relapse and shows that Compound 1 has neuroprotective properties.

FIG. 7 B shows axonal content in the spinal cord following treatment of relapsing EAE with Compound 1 mg/kg measured as neurofilament level adjusted for total protein content. EAE was induced with spinal cord homogenate in complete Freund's adjuvant on days 0 and 7 and a relapse was induced by re-immunisation with spinal cord homogenate in complete Freund's adjuvant at day 28. Animals were randomized according to RotaRod performance score at day 27 to receive either vehicle (Cremophor (Sigma, UK), alcohol, phosphate buffered saline 1:1;18) or 1 mg/kg i.p Compound 1 from day 33 p.i. just prior to the development of relapse at day 35 until day 47. Animals were killed and the spinal cords removed using hydrostatic pressure and axonal content measured using a quantitative neurofilament-specific ELISA. n=1 untreated, n=13 Compound 1 treated. Ratio of dephosphorylated (SMI-32 reactive) neurofilament to hyperphosphorylated (SMI-35 reactive) neurofilament as measured by ELISA in spinal cord homogenates from untreated post-relapse untreated animals; n=1 or Compound 11 mg/kg treated animals n=13 * P<0.001 adjusted for total protein level.

FIG. 8 shows the results from Example 10, in which the inhibition of $Ca^{2+}$ mediated PT pore formation was measure for Compounds 1, 3 and 4 and Reference Compound 1.

DETAILED DESCRIPTION OF THE INVENTION

Figure 1:
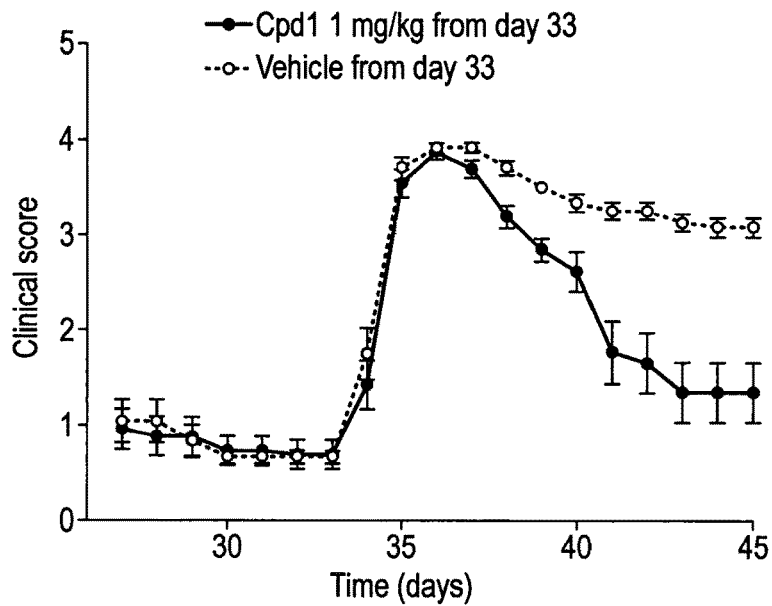
FIG. 1 shows the results from Example 2 in which experimental autoimmune encephalomyelitis (EAE) was induced in mice. The mice were injected daily intraperitoneally with either vehicle [ethanol cremophor:phosphate buffered saline (1:1:18)] or 1 mg/kg Compound 1 from day 33 shortly before the anticipated onset of signs of relapse.

Typically, one of $R_1$ and $R_1{}^*$ represents $-L_1Z_1$ and the other represents hydrogen, and $R_3$ represents hydrogen, $C_1$-$C_3$ alkyl or $C_2$-$C_4$ alkenyl. Alternatively, one of $R_1$ and $R_1{}^*$ represents methyl and the other represents hydrogen, and $R_3$ represents $-L_3Z_3$. Alternatively, one of $R_1$ and $R_1{}^*$ represents $-L_1Z_1$ and the other represents hydrogen, and $R_3$ represents $-L_3Z_3$.

Typically, $R_1$ represents methyl or $-L_1$-$Z_1$ and $R_1{}^*$ represents hydrogen. Accordingly, is preferred that (i) $R_1$ represents $-L_1Z_1$, $R_1{}^*$ represents hydrogen and $R_3$ represents hydrogen, $C_1$-$C_3$ alkyl or $C_2$-$C_4$ alkenyl, or (ii) $R_1$ represents methyl, $R_1{}^*$ represents hydrogen and $R_3$ represents $-L_3Z_3$, or (iii) $R_1$ represents $-L_1Z_1$, and $R_1{}^*$ represents hydrogen and $R_3$ represents $-L_3Z_3$.

Conjugates comprising one quinolinium moiety are preferred. Accordingly, it is particularly preferred that $R_1$ represents $-L_1Z_1$, $R_1{}^*$ represents hydrogen and $R_3$ represents hydrogen, $C_1$-$C_3$ alkyl or $C_2$-$C_4$ alkenyl. It is also particularly preferred that $R_1$ represents methyl, $R_1{}^*$ represents hydrogen and $R_3$ represents $-L_3Z_3$.

Typically, when $R_3$ does not represents $-L_3Z_3$, it represents hydrogen, methyl or $-CH_2CH=CH_2$, preferably hydrogen or $-CH_2CH=CH_2$. When $R_3$ does not represent hydrogen, there is a stereochemical centre at the 3' position. Conjugates of the invention are typically racemic at this position, but under some circumstances (R) stereochemistry or (S) at the 3' position, that is the position where the $R_3$ moiety is attached, is preferred.

Typically, A represents

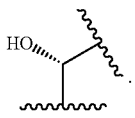

Typically, B represents methyl. Typically, $R_2$ represents ethyl. Typically, $R_4$ represents $-CH_2CH(CH_3)CH_3$.

Preferably, A represents

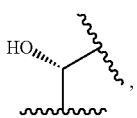

B represents methyl, $R_2$ represents ethyl and $R_4$ represents $-CH_2CH(CH_3)CH_3$.

Typically, the $C_1$-$C_6$ alkylene moiety which $L_1$ and $L_3$ independently represent is a $C_1$-$C_3$ alkylene moiety.

Typically, the $C_2$-$C_6$ alkenylene moiety which may $L_1$ and $L_3$ independently represent is a $C_3$-$C_5$ alkenylene moiety.

For the avoidance of doubt, the $-(CH_2CH_2O)_n(CH_2)_m-$ moiety which $L_1$ and $L_3$ may represent can be attached to $Z_1$ or $Z_3$ at either end of the $-(CH_2CH_2O)_n(CH_2)_m-$-moiety, ie. $Z-(CH_2CH_2O)_n(CH_2)_m-$ or $-(CH_2CH_2O)_n(CH_2)_m-Z$. Typically, n represents 1 or 2. Typically, m represents 0 or 2.

Preferably, $L_1$ represents a $C_1$-$C_6$ alkylene moiety, preferably a $C_1$-$C_3$ alkylene moiety, for example a $-CH_2CH_2-$ or $-CH_2CH_2CH_2-$ moiety.

Preferably, $L_3$ represents a $C_2$-$C_6$ alkenylene moiety, preferably a $C_3$-$C_5$ alkenylene moiety, for example a $-CH=CHCH_2-$, $-CH=CHCH_2CH_2-$, or $-CH=CHCH_2CH_2CH_2-$ moiety.

Typically, the quinolinium ring is unsubstituted or substituted by one to three, for example one or two, substituents selected from a halogen atom, a $C_1$-$C_6$ alkyl group, a $C_1$-$C_6$ haloalkyl group, a $-OR'$ group, a $-COOR'$ group, a $-CONR'R''$ group and a $-NR'R''$ group, wherein R' and R'' are the same or different and represent hydrogen or a $C_1$-$C_6$ alkyl group.

Typically, R' and R'' are the same or different and represent hydrogen or methyl.

Preferred substituents of the quinolinium ring are a halogen atom, a $C_1$-$C_6$ alkyl group, a $C_1$-$C_6$ haloalkyl group, a $-OR'$ group, or a $-NR'R''$ group, wherein R' and R'' are as defined above. Particularly preferred substituents of the quinolinium ring are a $C_1$-$C_6$ haloalkyl group (such as $-CF_3$), a $-OR'$ group (such as $-OH$), or a $-NR'R''$ group (such as $-NMe_2$).

For the avoidance of doubt, the quinolinium ring which $Z_1$ and $Z_3$ independently represent is a moiety of formula (II):

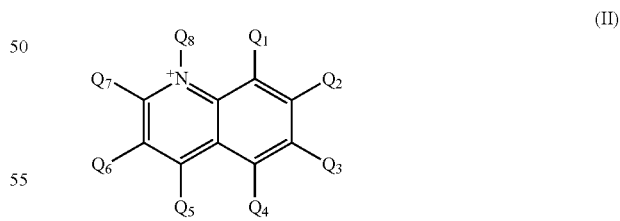

(II)

in which: $Q_1$ to $Q_7$ independently represent a direct bond to $L_1$ or $L_3$, a hydrogen atom, a halogen atom, a $C_1$-$C_6$ alkyl group, a $C_1$-$C_6$ haloalkyl group, a $-OR'$ group, a $-COOR'$ group, a $-CONR'R''$ group or a $-NR'R''$ group, wherein R' and R'' are the same or different and represent hydrogen or a $C_1$-$C_6$ alkyl group; and $Q_8$ represents a direct bond to $L_1$ or $L_3$, a hydrogen atom or a $C_1$-$C_6$ alkyl group; provided that only one of $Q_1$ to $Q_8$ represents a direct bond to $L_1$ or $L_3$.

Typically, the quinolinium ring is attached to $L_1$ or $L_3$ by a direct bond between $L_1$ or $L_3$ and the nitrogen atom of the quinolinium ring. Accordingly, $Z_1$ and $Z_3$ are typically connected to $L_1$ and $L_3$ respectively by a direct bond to the nitrogen atom (ie. where $Q_8$ represents a direct bond). Thus, $Z_1$ and $Z_3$ typically independently represent a moiety of formula (II*):

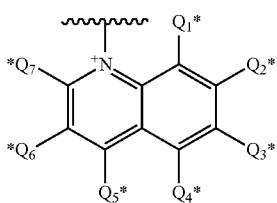
(II*)

in which $Q_1^*$ to $Q_7^*$ independently represent a hydrogen atom, a halogen atom, a $C_1$-$C_6$ alkyl group, a $C_1$-$C_6$ haloalkyl group, a —OR' group, a —COOR' group, a —CONR'R" group or a —NR'R" group, wherein R' and R" are as defined above.

Preferably $Q_1^*$ to $Q_7^*$ independently represent a hydrogen atom, a halogen atom, a $C_1$-$C_6$ alkyl group, a $C_1$-$C_6$ haloalkyl group, a —OR' group, or a —NR'R" group, wherein R' and R" are as defined above. More preferably, $Q_1^*$ to $Q_7^*$ independently represent a hydrogen atom, a $C_1$-$C_6$ haloalkyl group (such as —$CF_3$), a —OR' group (such as —OH), or a —NR'R" group (such as —$NMe_2$).

As discussed above, the quinolinium ring is typically unsubstituted or substituted with one to three, for example one or two substituents. Thus, typically four to seven of $Q_1^*$ to $Q_7^*$ represent hydrogen, for example five of $Q_1^*$ to $Q_7^*$ represent hydrogen (in which case the quinolinium carries two substituents), or six of $Q_1^*$ to $Q_7^*$ represent hydrogen (in which case the quinolinium carries one substituent), or all seven of $Q_1^*$ to $Q_7^*$ represent hydrogen (in which case the quinolinium is unsubstituted).

Preferred examples of quinolinium rings are moieties of formula (II*a), (II*b) and (II*c):

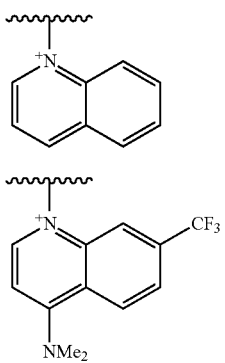
(II*a)

(II*b)

(II*c)

Alternatively, the quinolinium ring may be attached to $L_1$ or $L_3$ by a direct bond between $L_1$ or $L_3$ and an available carbon atom of the quinolinium ring. Accordingly, $Z_1$ and $Z_3$ may be connected to $L_1$ and $L_3$ respectively by a direct bond to an available carbon atom in the quinolinium ring (ie. where one of $Q_1$ to $Q_7$ represents a direct bond). In that instance, $Q_8$ represents a hydrogen atom or a $C_1$-$C_6$ alkyl group, preferably a hydrogen atom or a methyl or ethyl group. The $Q_1$ to $Q_7$ moieties which are not a direct bond are preferably as defined above for $Q_1^*$ to $Q_7^*$.

In a preferred embodiment:
$R_1$ represents -$L_1Z_1$, $R_1^*$ represents hydrogen and $R_3$ represents hydrogen or —$CH_2CH$=$CH_2$, preferably hydrogen;
A represents

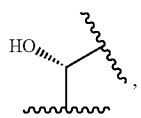

B represents methyl, $R_2$ represents ethyl and $R_4$ represents —$CH_2CH(CH_3)CH_3$;
$L_1$ represents a $C_1$-$C_6$ alkylene moiety, preferably a $C_1$-$C_3$ alkylene moiety; and
$Z_1$ represents a moiety of formula (II*), (II*a), (II*b) or (II*c) as defined above.

In a further preferred embodiment:
$R_1$ represents methyl, $R_1^*$ represents hydrogen and $R_3$ represents -$L_3Z_3$;
A represents

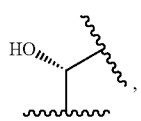

B represents methyl, $R_2$ represents ethyl and $R_4$ represents —$CH_2CH(CH_3)CH_3$;
$L_3$ represents a $C_2$-$C_6$ alkenylene moiety, preferably a $C_3$-$C_5$ alkenylene moiety; and
$Z_3$ represents a moiety of formula (II*), (II*a), (II*b) or (II*c) as defined above.

Particularly preferred conjugates of the invention are Compounds 1 to 6 depicted below and pharmaceutically acceptable salts thereof:

Compound 1
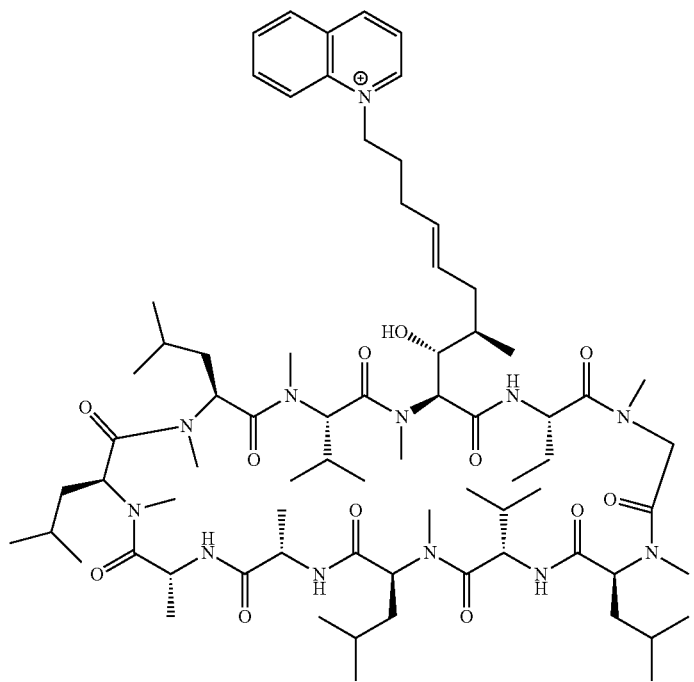
Compound 2
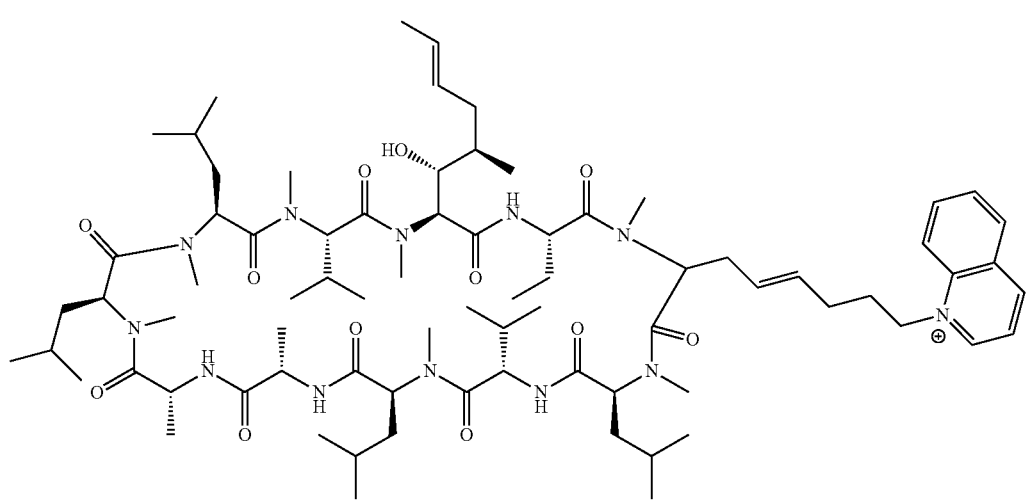

-continued
Compound 3
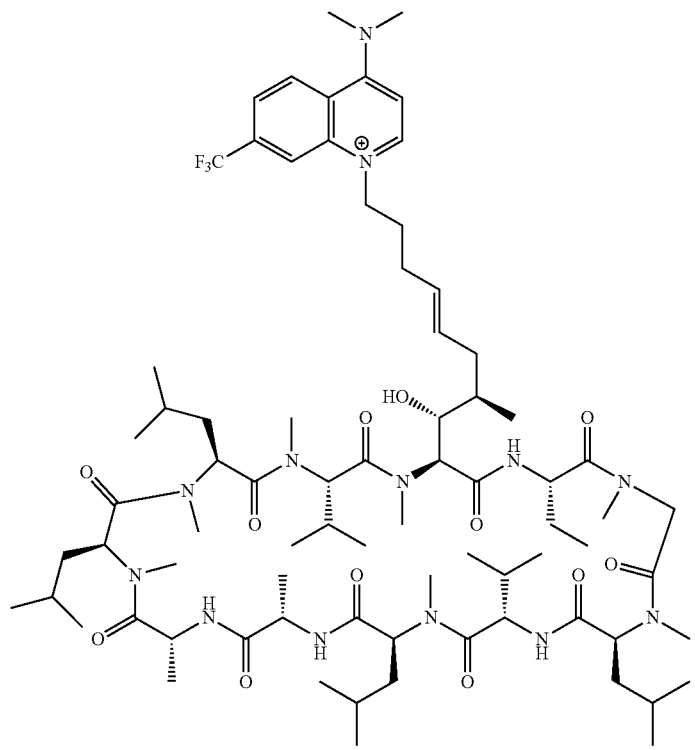
Compound 4
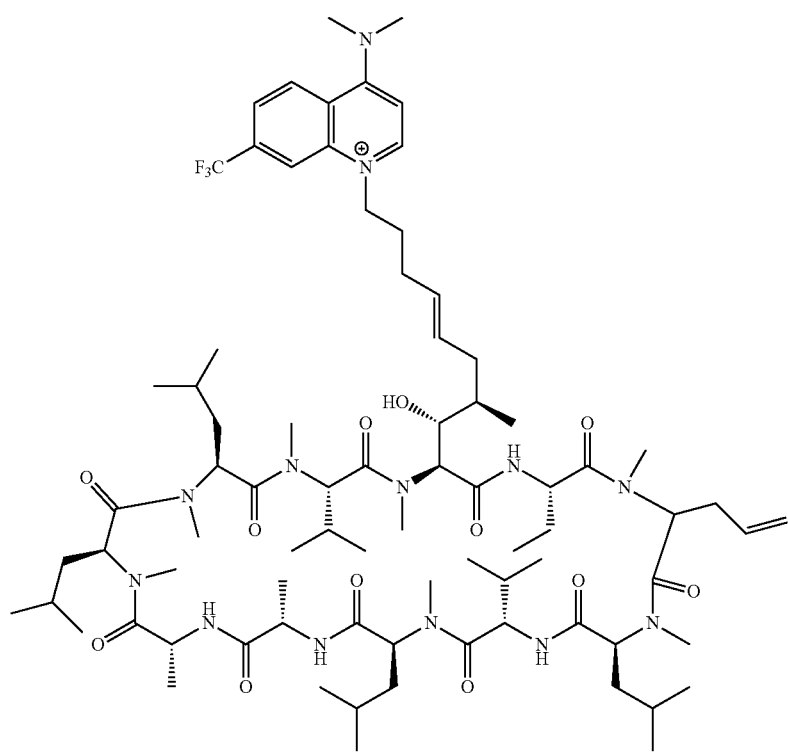

Compound 5

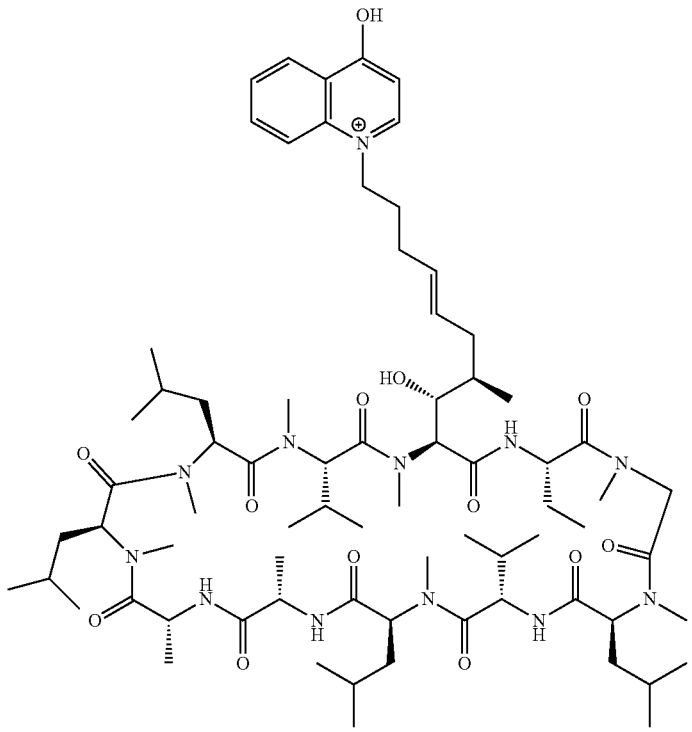

Compound 6

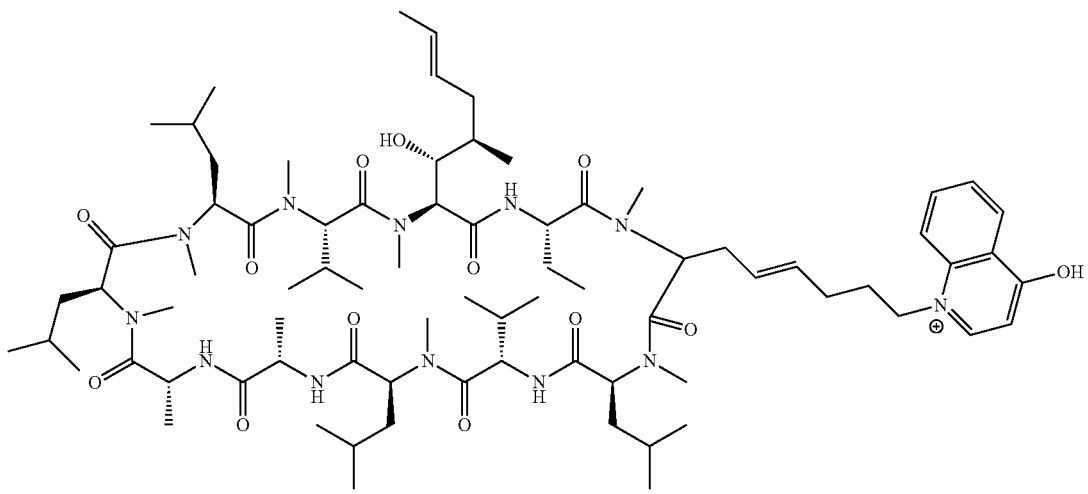

As used herein, a $C_1$-$C_6$ alkyl group is straight or branched and is typically a $C_1$-$C_3$ alkyl group. Preferred $C_1$-$C_6$ alkyl groups include, for example, methyl, ethyl, propyl, isopropyl, butyl, isobutyl, tert-butyl, pentyl and hexyl.

As used herein, a $C_1$-$C_6$ alkylene group is a said $C_1$-$C_6$ alkyl group which is divalent.

As used herein, a $C_2$-$C_4$ alkenyl group is straight or branched and is typically a $C_2$-$C_3$ alkenyl group. A $C_2$-$C_4$ alkenyl group typically contains one carbon-carbon double bond. The carbon-carbon double bond can have cis or trans configuration, with trans preferred. Preferred $C_2$-$C_4$ alkenyl group include —CH=$CH_2$, —$CH_2$CH=$CH_2$ and —$CH_2CH_2$CH=$CH_2$ As used herein, a $C_2$-$C_6$ alkenylene group is a divalent moiety which may be straight or branched and is typically a $C_3$-$C_5$ alkenylene group. A $C_2$-$C_6$ alkenylene group typically contains one carbon-carbon double bond. The carbon-carbon double bond can have cis or trans configuration, with trans preferred.

As used herein, a halogen is typically chlorine, fluorine, bromine or iodine and is preferably chlorine, bromine or fluorine.

As used herein, a $C_1$-$C_6$ haloalkyl group is a said $C_1$-$C_6$ alkyl substituted by one or more said halogen atoms. Typically, it is substituted by 1, 2 or 3 said halogen atoms. Particularly preferred haloalkyl groups are —$CF_3$ and —$CCl_3$.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines or heterocyclic amines.

The conjugates of the invention may be prepared by standard methods known in the art. Cyclosporin is a known compound which is commercially available, and can then be linked to mitochondrial targeting groups using standard techniques known in the art, such as those described in the Examples that follow.

The conjugates of the invention are useful in the treatment or prevention of diseases or disorders susceptible to amelioration by inhibition of cyclophilin D, particularly in humans. Thus, the conjugates of the invention may preferably be used to improve the condition of a patient who has suffered from, is suffering from or is at risk of suffering from ischaemia/reperfusion injury. In particular, the compounds of the invention may be used in the treatment of cerebral or myocardial ischaemia/reperfusion injury. Neurodegenerative diseases, such as Alzheimer's disease and multiple sclerosis may also be treated by inhibition of cyclophilin D.

Preferably said disease or disorder susceptible to amelioration by inhibition of cyclophilin D is ischaemia/reperfusion injury or a neurodegenerative disease. Examples of neurodegenerative diseases include Alzheimer's disease and multiple sclerosis. Most preferably however said disease or disorder susceptible to amelioration by inhibition of cyclophilin D is ischaemia/reperfusion injury. Multiple sclerosis is also particularly preferred.

The conjugates of the invention may be administered to humans in various manners such as oral, rectal, vaginal, parenteral, intramuscular, intraperitoneal, intraarterial, intrathecal, intrabronchial, subcutaneous, intradermal, intravenous, nasal, buccal or sublingual routes of administration. The particular mode of administration and dosage regimen will be selected by the attending physician, taking into account a number of factors including the age, weight and condition of the patient.

The pharmaceutical compositions that contain the conjugates of the invention as an active principal will normally be formulated with an appropriate pharmaceutically acceptable excipient, carrier or diluent depending upon the particular mode of administration being used. For instance, parenteral formulations are usually injectable fluids that use pharmaceutically and physiologically acceptable fluids such as physiological saline, balanced salt solutions, or the like as a vehicle. Oral formulations, on the other hand, may be solids, e.g. tablets or capsules, or liquid solutions or suspensions.

Compositions may be formulated in unit dosage form, i.e., in the form of discrete portions containing a unit dose, or a multiple or sub-unit of a unit dose.

The amount of the conjugate of the invention that is given to a patient will depend upon the activity of the particular conjugate in question. Further factors include the condition being treated, the nature of the patient under treatment and the severity of the condition under treatment. The timing of administration of the conjugate should be determined by medical personnel, depending on whether the use is prophylactic or to treat ischemia/reperfusion injury. As a skilled physician will appreciate, and as with any drug, the conjugate may be toxic at very high doses. For example, the agent may be administered at a dose of from 0.01 to 30 mg/kg body weight, such as from 0.1 to 10 mg/kg, more preferably from 0.1 to 5 mg/kg body weight. A preferred dosage is about 1 mg/kg.

The conjugates of the invention may be given alone or in combination with one or more additional active agents useful for treating a disease or disorder susceptible to amelioration by inhibition of cyclophilin D, such as ischaemia/reperfusion injury or a neurodegenerative disease. Two or more active agents are typically administered simultaneously, separately or sequentially. The active ingredients are typically administered as a combined preparation.

The conjugates of the invention can also be used as reagents. For example, they are useful in non-therapeutic experimental procedures in which selective inhibition of cyclophilin D is required. The conjugates of the invention are therefore useful as laboratory reagents for assessing the involvement of cyclophilin D in cellular processes, such as cell death. No such reagents are currently available. Typically, said non-therapeutic experimental procedure is an assay.

The following Examples illustrate the invention.

EXAMPLES

Materials and Methods

All commercially available solvents and reagents were used without further treatment as received unless otherwise noted. NMR spectra were measured with a Bruker DRX 500 or 600 MHz spectrometer; chemical shifts are expressed in ppm relative to TMS as an internal standard and coupling constants (J) in Hz. LC-MS spectra were obtained using a Waters ZQ2000 single quadrupole mass spectrometer with electrospray ionisation (ESI), using an analytical C4 column (Phenomenex Gemini, 50×3.6 mm, 5 μm) and an AB gradient of 50-95% for B at a flow rate of 1 mL/minute, where eluent A was 0.1:5:95 formic acid/methanol/water and eluent B was 0.1:5:95 formic acid/water/methanol. High resolution mass spectra were acquired on a Waters LCT time of flight mass spectrometer with electrospray ionisation (ESI) or chemical ionization (CI).

Synthesis of Intermediate 1:
1-(pent-4-enyl)quinolinium

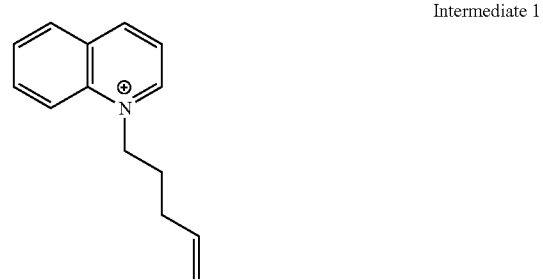

Intermediate 1

To a solution of quinoline (1 g, 7.74 mmol) in EtOAc was added 5-bromo-pent-1-ene (1.27 g, 8.51 mmol) and this mixture was heated to reflux overnight. The mixture was allowed to cool before concentration under reduced pressure. Intermediate 1 was isolated as a light brown oil (1.54 g, 99%).

LCMS (m/z): [MH]$^+$ calcd. for $C_{14}H_{16}N+$, 198.29; found 198.10.

Synthesis of Compound 1: [Gly-(1S,2R,E)-8-quinolinium-1-hydroxy-2-methyloct-4-ene]¹ CsA Compound 1

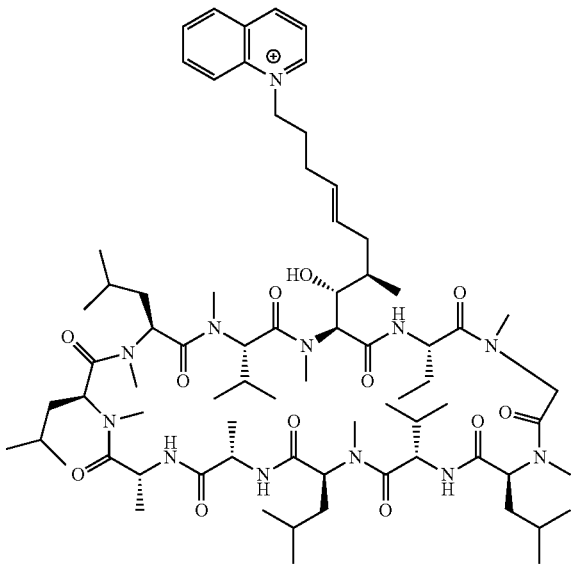

To a solution of Cyclosporin A (75 mg, 0.06 mmol) in DCM (2 mL) was added Intermediate 1, 1-(pent-4-en-1-yl)quinolinium (23 mg, 0.072 mmol) and Hoveyda-Grubbs $2^{nd}$ generation catalyst (7 mg, 0.01 mmol, 17 mol %). The reaction was stirred in the microwave at 90° C. for 30 minutes and then allowed to cool. Triethylamine was added to the mixture and then stirred overnight with excess $P(CH_2OH)_3$ to coordinate the ruthenium catalyst. This was then washed away with brine and water before the mixture was passed through a Stratospheres PL Thiol MP SPE cartridge (polymer Lab, Varian Inc) to remove any remaining catalyst. The crude product was purified by flash reverse-phase chromatography (MeOH:H₂O:formic acid) to give Compound 1 as a brown solid (15 mg, 17%).

HRMS (m/z): $[MH]^+$ calcd. for $C_{65}H_{115}NO_{12}$, 1358.84; found 1357.95.

Synthesis of Intermediate 2: [Sar-Allyl]³ CsA

Intermediate 2

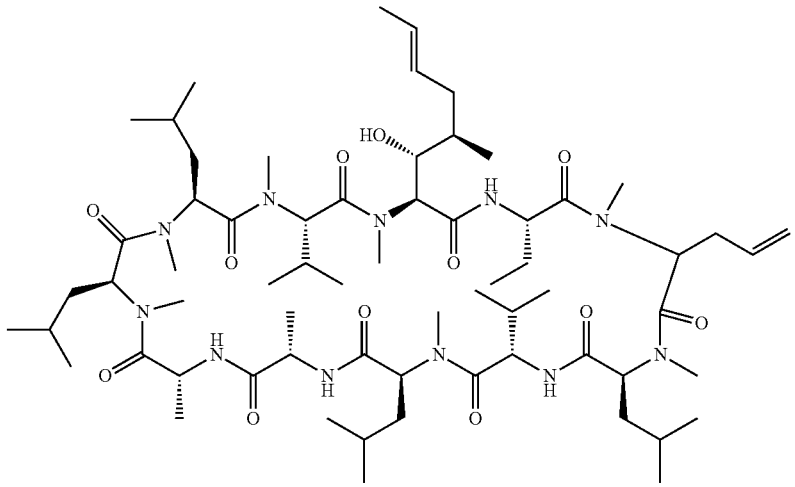

To a stirred solution of 1.8M lithium diisopropylamide (39 mL, 70 mmol) in anhydrous THF at −10° C. was added dropwise a cooled solution of Cyclosporin A (6 g, 5 mmol) and lithium chloride (3.81 g, 89 mmol) in THF. The mixture was stirred at this temperature for an hour before the dropwise addition of a solution of allyl bromide (0.755 ml, 8.7 mmol) in THF. After a further 3 hours stirring at −5° C. the reaction was quenched by the addition of 5% acetic acid in methanol solution.

The mixture was concentrated under reduced pressure before dissolution in DCM and water. The DCM layer was separated and the aqueous layer was extracted twice with DCM. The organic fractions were combined, dried over magnesium sulphate and concentrated under reduced pressure. The product was purified by flash silica chromatography (0-20% acetone:DCM gradient) to give Intermediate 2 as an off-white solid (1.144 g, 18%).

HRMS (m/z): $[MH]^+$ calcd. for $C_{65}H_{115}N_{11}O_{12}$, 1242.88; found 1242.89.

Synthesis of Compound 2: [Sar-(E)-Hexen-2-yl 6-quinolinium]³ CsA

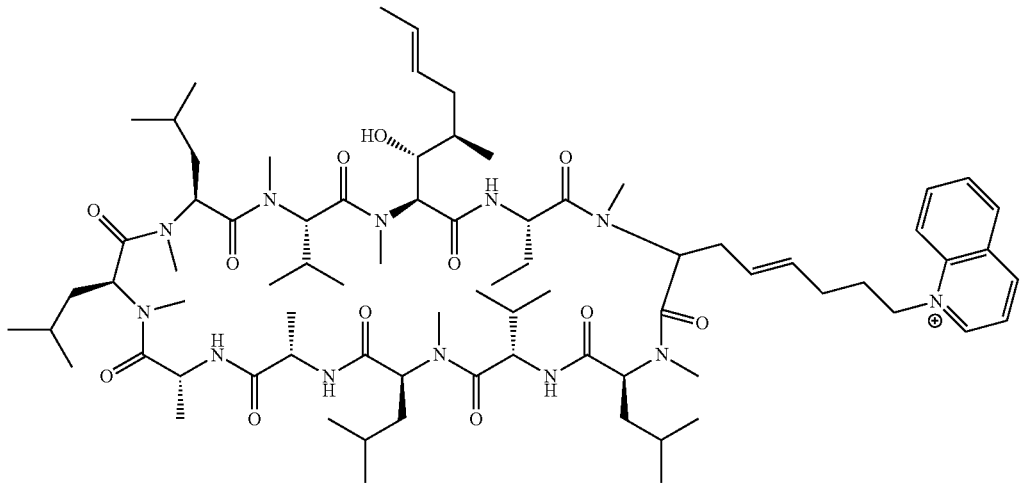

Compound 2

Compound 2 was prepared from Intermediate 1 and Intermediate 2 using the method described above for the synthesis of Compound 1.

The crude product was purified by flash reverse-phase chromatography (MeOH:H$_2$O:formic acid) to give Compound 2 as a dark brown solid (1.144 g, 18%).

HRMS (m/z): [MH]$^+$ calcd. for C$_{65}$H$_{115}$N$_{11}$O$_{12}$, 1412.93; found 1411.82.

Synthesis of Intermediate 3: 4-(dimethylamino)-1-(pent-4-en-1-yl)-7-(trifluoromethyl)quinolinium

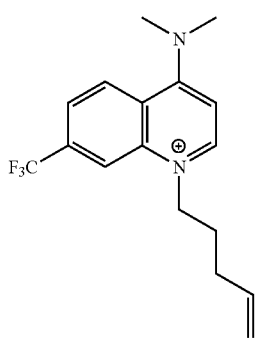

Intermediate 3

To a solution of 4-dimethylamino-7-(trifluoromethyl) quinoline (1.98 g, 6.4 mmol) in EtOAc was added 5-bromopent-1-ene (1.6 g, 10.7 mmol) and this mixture was heated to reflux overnight. The mixture was allowed to cool before concentration under reduced pressure. Intermediate 3 was isolated as a brown oil (2.41 g, 94%).

LCMS (m/z): [MH]$^+$ calcd. for C$_{17}$H$_{20}$F$_3$N$_2$+, 309.36; found 309.10.

$^1$H NMR (600 MHz, CDCl$_3$) δ 9.52-9.44 (m, 1H), 8.50 (d, J=8.9 Hz, 1H), 8.03 (s, 1H), 7.84 (dd, J=8.9, 1.3 Hz, 1H), 7.33 (dd, J=11.8, 7.6 Hz, 1H), 5.83 (ddt, J=17.0, 10.2, 6.7 Hz, 1H), 5.20-5.03 (m, 2H), 4.86-4.63 (m, 2H), 3.60 (s, 6H), 2.33-2.19 (m, 2H), 2.15-2.00 (m, 2H).

Synthesis of Compound 3: [Gly(1S,2R,E)-10-(4-dimethylamino-7-trifluoromethylquinolinium)1-hydroxy-2-methyldec-4-enoic acid]$^1$ CsA

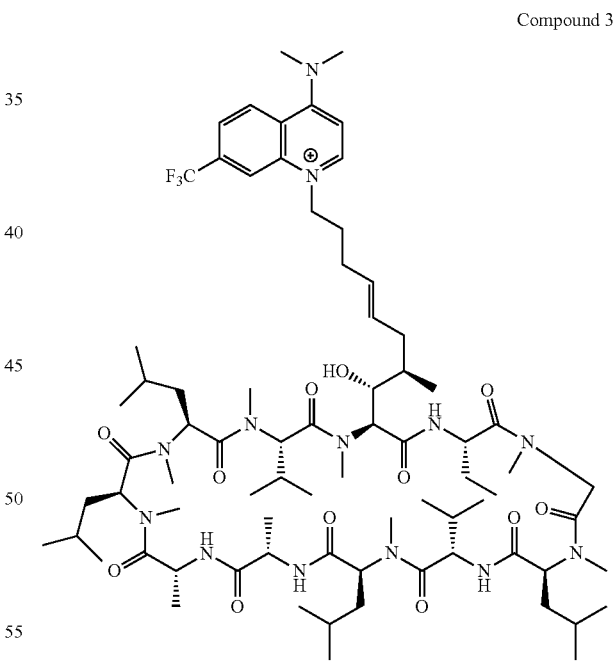

Compound 3

Compound 3 was prepared from Cyclosporin A and Intermediate 3 using the method described above for the synthesis of Compound 1. The crude product was purified by flash reverse-phase chromatography (MeOH:H$_2$O:formic acid) to give Compound 3 as a brown solid (32 mg, 26%).

HRMS (m/z): [MH]$^+$ calcd. for C$_{76}$H$_{125}$F$_3$N$_{13}$O$_{12}$+, 1469.91; found 1468.89.

Synthesis of Compound 4

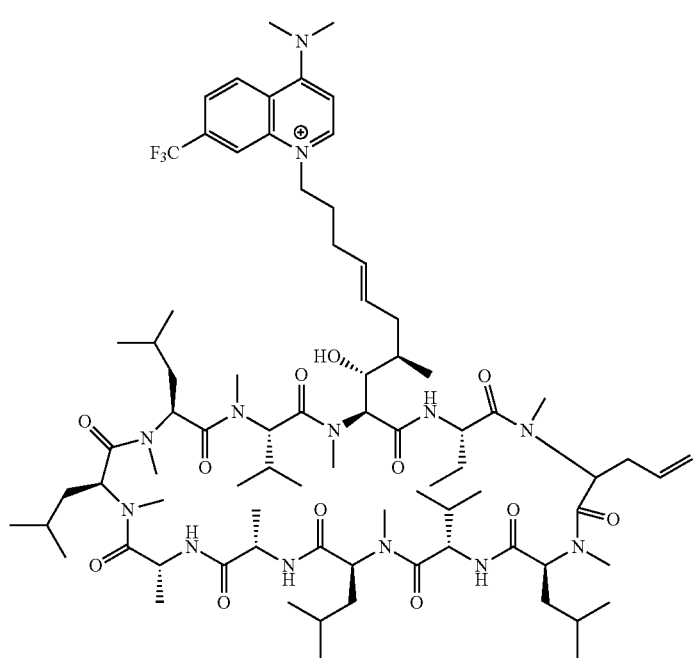

Compound 4

Compound 4 was prepared using analogous methods tot those described above. The crude product was purified by flash reverse-phase chromatography (MeOH:H$_2$O:formic acid) to give Compound 4 as a brown solid (15 mg, 17%).

HRMS (m/z): [MH]$^+$ calcd. for $C_{79}H_{129}F_3N_{13}O_{12}$+, 1509.94; found 1510.04

Synthesis of Intermediate 4: 4-hydroxy-1-(pent-4-enyl)quinolinium

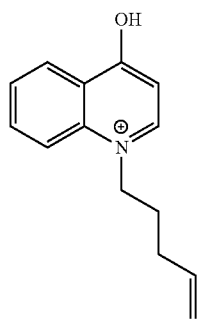

Intermediate 4

To a solution of 4-methoxyquinoline (550 mg, 3.45 mmol) in EtOAc was added 5-bromo-pent-1-ene (1.55 g, 10.35 mmol) and this mixture was heated to reflux overnight. The mixture was allowed to cool before concentration under reduced pressure. The crude product was purified by flash silica chromatography (100:8:1 DCM:MeOH:NH$_3$). Intermediate 4 was isolated as a pale yellow oil (420 mg, 53%).

$^1$H NMR (600 MHz, CDCl$_3$) δ 8.48 (d, J=8.1 Hz, 1H), 7.67 (dd, J=8.4, 7.2 Hz, 1H), 7.52 (d, J=7.5 Hz, 1H), 7.47-7.35 (m, 2H), 6.27 (d, J=7.7 Hz, 1H), 5.99-5.72 (m, 2H), 5.10 (dd, J=14.4, 5.4 Hz, 2H), 4.12 (t, J=7.3 Hz, 2H), 2.16 (q, J=7.0 Hz, 2H), 2.02-1.92 (m, 2H).

Synthesis of Compound 5: [Gly-(1S,2R,E)-8-(4-hydroxyquinolinium)-1-hydroxy-2-methyloct-4-ene]$^1$ CsA

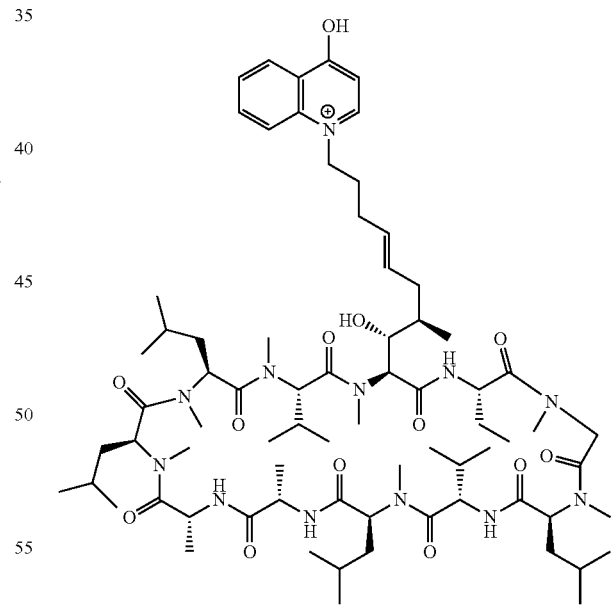

Compound 5

Compound 5 was prepared from Cyclosporin A and Intermediate 4 using the method described above for the synthesis of Compound 1.

The crude product was purified by flash silica chromatography (200:8:1 DCM:MeOH:NH3) to give Compound 5 as a brown solid (23 mg, 20%).

HRMS (m/z): [MH]$^+$ calcd. for $C_{73}H_{121}N_{12}O_{13}$+, 1374.84; found 1373.83.

Synthesis of Compound 6: [Sar-(E)-Hexen-2-yl-6-(4-hydroxy)quinolinium]³ CsA

Compound 6

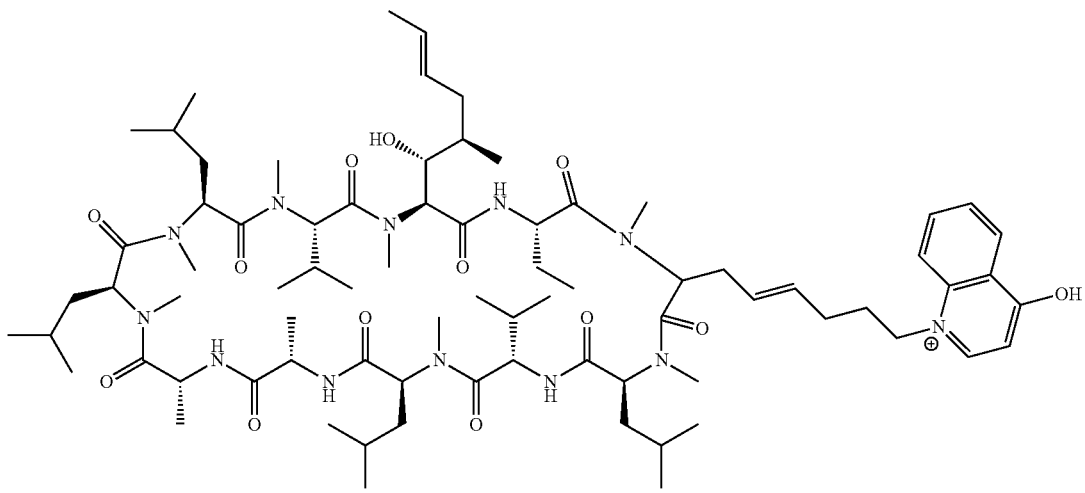

Compound 6 was prepared from Intermediate 2 and Intermediate 4 using the method described above for the synthesis of Compound 1. The crude product was purified by flash silica chromatography (200:8:1 DCM:MeOH:NH3)) to give Compound 6 as a dark brown solid (11 mg, 13%).

HRMS (m/z): [MH]⁺ calcd. for $C_{77}H_{127}N_{12}O_{13}$+, 1428.93; found 1428.01.

Synthesis of Intermediate 5:
6-Chloro-3-nitro-2-aminopyridine

Intermediate 5

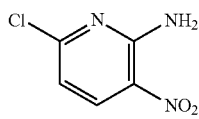

To a flask charged with 2,6-dichloro-3-nitropyridine (3 g, 15.5 mmol) was added 2M ammonia in isopropanol solution (18 ml, 36 mmol) and this mixture was stirred overnight at room temperature. The reaction was driven to completion by the addition of ammonia solution (aq). The resulting precipitate was filtered off, washed with water and then dried over vacuum for an hour. Intermediate 5 was isolated as a fluffy yellow powder (1.38 g, 51%).

LCMS (m/z): [MH]⁺ calcd. for $C_5H_4Cl_1N_3O_2$, 173.56; found 174.00.

Synthesis of Intermediate 6: N²-(4-fluorobenzyl)-5-nitropyridine-2,6-diamine

Intermediate 6

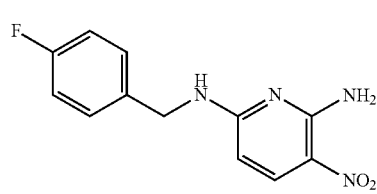

To a solution of Intermediate 5 (500 mg, 2.9 mmol) in isopropanol was added 4-fluorobenzylamine (463 μl, 4.06 mmol) and triethylamine (805 μl, 5.8 mmol). This mixture was stirred at 90° C. for 40 minutes in the microwave. Water was added to the mixture and the resulting precipitate was filtered off, washed with water and then dried over vacuum for an hour. Intermediate 6 was isolated as a bright yellow solid (661 mg, 88%).

LCMS (m/z): [MH]⁺ calcd. for $C_{12}H_{11}FN_4O_2$, 262.24; found 263.00.

Synthesis of Intermediate 7: N⁶-(4-fluorobenzyl)pyridine-2,3,6-triamine

Intermediate 7

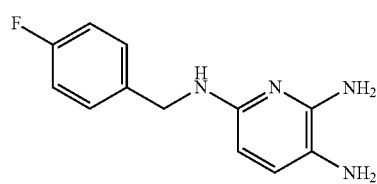

To a solution of Intermediate 6 (300 mg, 1.15 mmol) in ethanol was added tin (II) chloride dihydrate (1.29 g, 5.72 mmol). This mixture was heated to reflux before the dropwise addition of a solution of sodium borohydride (216 mg, 5.72 mmol) in ethanol. The resulting mixture was refluxed for 90 minutes and allowed to cool before filtration through celite and concentration under reduced pressure. Intermediate 7 was isolated as an orange residue (230 mg, 86%).

LCMS (m/z): [MH]$^+$ calcd. for $C_{12}H_{13}FN_4$, 232.26; found 233.10.

Synthesis of Intermediate 8: N-(2-amino-6-((4-fluorobenzyl)amino)pyridin-3-yl)pent-4-enamide Intermediate 8

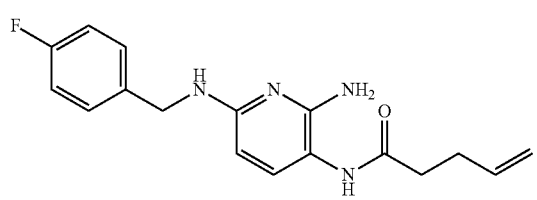

To a solution of Intermediate 7 (300 mg, 1.14 mmol) in DCM stirring at 0° C. was added triethylamine (240 µl, 1.71 mmol) followed by the dropwise addition of 4-pentenoyl chloride (140 µl, 1.25 mmol). This mixture was stirred at 0° C. for 2 hours after which the solution was washed with 2M HCl solution and brine before drying over MgSO4 and concentrating under reduced pressure. The crude product was purified by flash silica chromatography (5% MeOH in DCM) to give Intermediate 8 as a pale yellow solid (195 mg, 54%).

LCMS (m/z): [MH]$^+$ calcd. for $C_{17}H_{19}FN_4O$, 314.36; found 315.10.

Synthesis of Reference Compound 1: [Gly-(1S,2R,E)-7-(flupirtine)-1-hydroxy-2-methyloct-4-enamide]$^1$ CsA Reference Compound 1

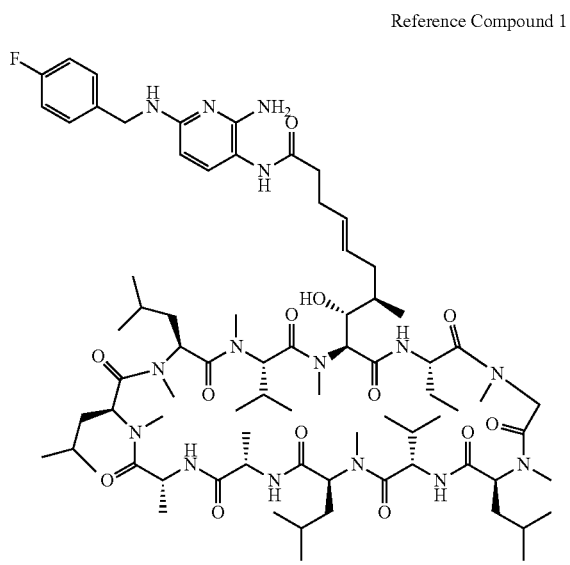 [SMILES: CC[C@@H]1NC(=O)[C@H]([C@H](O)[C@H](C)C/C=C/CCC(=O)Nc2ccc(NCc3ccc(F)cc3)nc2N)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]

Reference Compound 1 was prepared from Cyclosporin A and Intermediate 7 using the method described above for the synthesis of Compound 1. The crude product was purified by flash reverse-phase chromatography (MeOH:H$_2$O:formic acid) to give Reference Compound 1 as a dark blue solid (26 mg, 21%).

HRMS (m/z): [MH]$^+$ calcd. for $C_{76}H_{124}FN_{15}O_{13}$, 1474.92; found 1474.95.

Example 1—Cyclophilin D Enzyme Assay

A competitive fluorescence polarization assay (FP-assay) was used. The assay uses a fluorescein-labeled CsA, the synthesis of which is described below, which competes for binding to Cylophilin D (CypD) with an unlabeled inhibitor.

Polarization was determined by measuring the ratios between parallel and perpendicular polarized light and calculated as described by Roehrl et al 2004.

Titration of a single probe concentration against different enzyme concentrations was used to determine the dissociation constant (Kd) (Nikolovska et al 2004). The inhibitor constant (Ki) was calculated with the equation shown below in Equation A. (Nikolovska et al 2004).

$$K_i = \frac{[L_{50}]}{\left(\frac{[L^*_{50}] + [R_o]}{K_d} + 1\right)}$$

Equation A: $K_i$ is the inhibitor constant, $L_{50}$ is IC$_{50}$, $L^*_{50}$ is the concentration of free labeled ligand at 50% inhibition, $R_0$ is concentration of protein at 0% inhibition, $K_d$ dissociation constant.

Measurement of Ki for Compounds 1 to 6

Assays were conducted in 384-black low flange non-binding microtiter plates (Corning Inc., Tewksbury, Md., USA). A total solution of 80 µL was used consisting of 3 components, fluorescent cyclosporine probe (FP-CsA) 45 nM, enzyme 40 nM, test compound (10-10000 nM). Three replicates were used for this experiment. Controls that were used in this experiment were, a blank with Hepes buffer, control with just probe, positive control with probe and enzyme and a reference control of FP-CsA to CsA and enzyme. DMSO % in total solution should remain lower than 1%.

The $K_i$ values measured for Compounds 1 to 6 are set out below in Table 1.

TABLE 1

| Test compound | $K_i$ for cylophilin D binding (nM) |
| --- | --- |
| Compound 1 | 28 |
| Compound 2 | 125 |
| Compound 3 | 24 |
| Compound 4 | 73 |
| Compound 5 | 64 |
| Compound 6 | 46 |

Preparation of the Fluorescein Labelled Cyclosporine (FP-CsA)

The fluorescein labelled cyclosporine (FP-CsA) was prepared according to the scheme set out below.

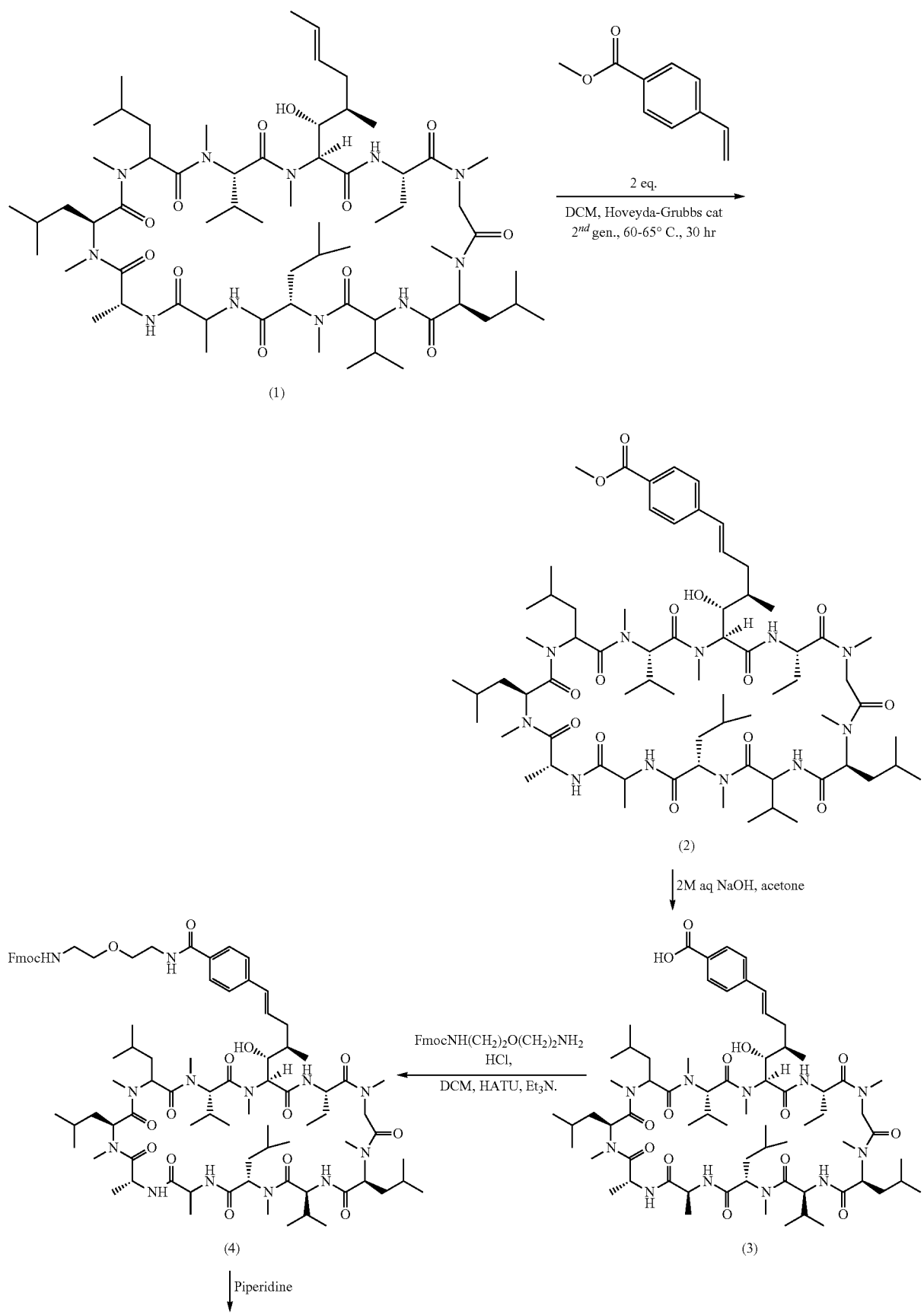

-continued

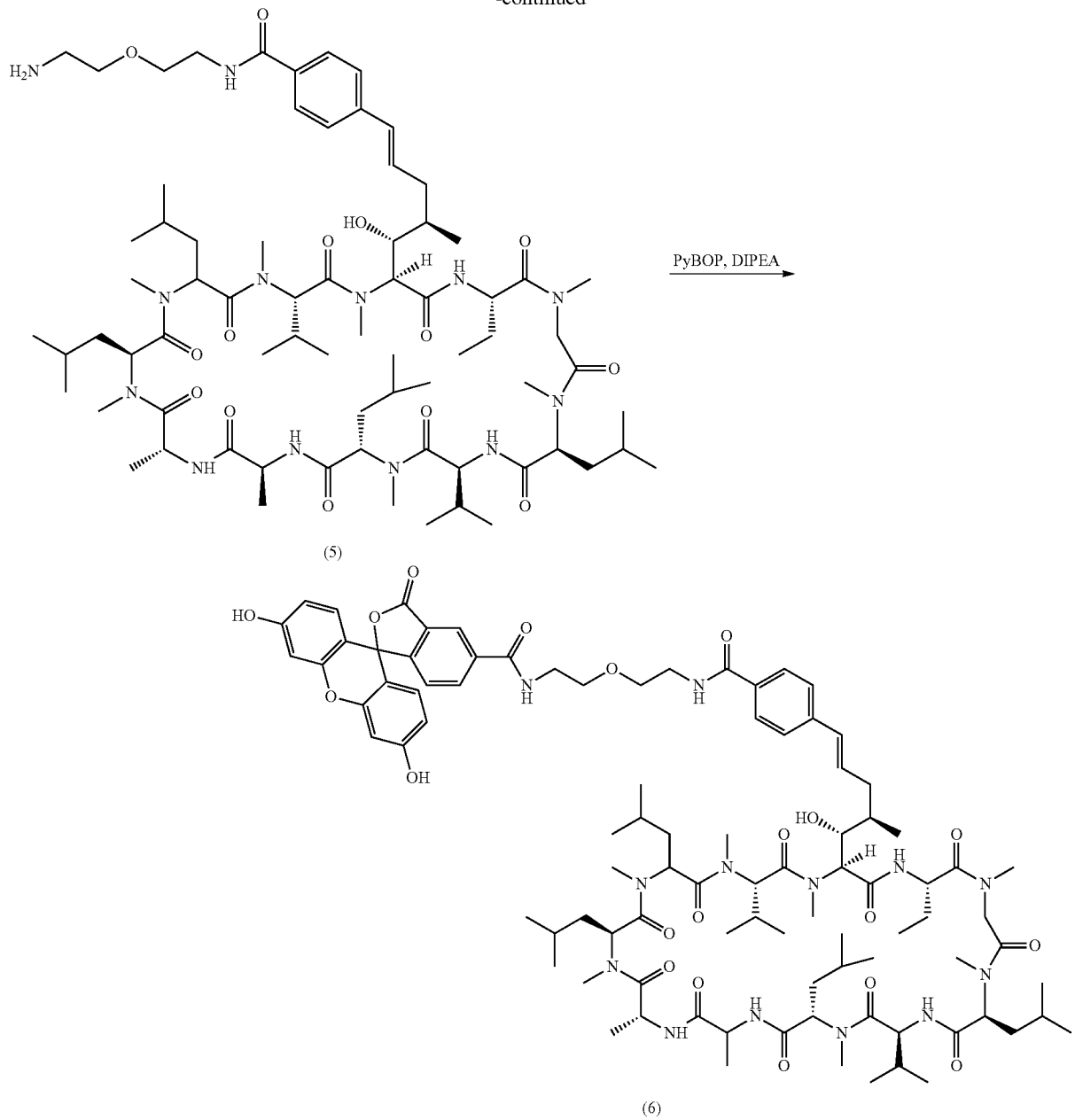

Formation of the Vinyl Methyl Ester Derivative (2) from Cyclosporine A (1).

A solution of cyclosporine A (1.00 g, 0.832 mmol), methyl-4-vinylbenzoate (270 mg, 1.665 mmol) and Hoveyda-Grubbs $2^{nd}$ generation catalyst (20 mg, 0.032, 4%) in dichloromethane (4 ml) was stirred at reflux (60° C.) under nitrogen for 48 hours. T.l.c. analysis (acetone:cyclohexane, 1:1) of the reaction mixture showed the presence of the product ($R_f$ 0.63) and complete consumption of the cyclosporine A starting material ($R_f$ 0.65). LCMS analysis also confirmed the presence of the product. The reaction mixture was pre-absorbed on silica gel and purified by flash column chromatography (ethyl acetate:cyclohexane, 1:1 to ethyl acetate to ethyl acetate:methanol, 10%) and the solvent removed in vacuo to give a grey solid. The grey solid was then further purified by removing the Grubbs-Hoveida catalyst by letting it through an SPE-thiol column (eluant: methanol). The solvent was removed in vacuo to give the corresponding methyl ester as a white crystalline solid (950 mg, 86.4%).

HRMS (TOF MS ES$^+$): found 1344.8726 [M+Na]$^+$ $C_{69}H_{115}N_{11}O_{14}Na$ requires 1344.8523.

Formation of the Vinyl Acid Derivative (3)

The methyl ester 2 (260 mg, 0.196 mMol) was stirred in acetone (4 mL) and an aqueous solution of sodium hydroxide (2M, 2 mL). After 19 hours a white precipitate had formed and T.l.c. analysis (acetone:cyclohexane, 1:1) showed the presence of one product ($R_f$ 0.17) and some residual starting material/impurity ($R_f$ 0.31). The acetone was removed from the reaction mixture and the aqueous layer left behind was washed with ethyl acetate. The aqueous layer was acidified with an aqueous solution of hydrochloric acid (1M) and washed again with ethyl acetate. The collected ethyl acetate layers were dried (magnesium sulfate), filtered and concentrated in vacuo to give a white/pale brown hygroscopic solid which was then diluted in acetonitrile and filtered again (eluant acetonitrile). The filtrate was finally concentrated in vacuo to give the acid derivative 3 (220 mg, 86%) as a white/pale brown hygroscopic solid.

HRMS (TOF MS ES$^+$): found 1330.8366 [M+Na]$^+$ $C_{68}H_{113}N_{11}O_{14}Na$ requires 1330.8173.

Synthesis of Fmoc Protected Intermediate (4)

HATU coupling reagent (230 mg, 0.6037 mMol) was added to a solution of the CsA acid 3 derivative (395 mg, 0.3018 mMol), chloroform (10 mL) and triethylamine (168 µL) which had been stirring for 5 minutes under an atmosphere of nitrogen at room temperature. After a further 5 minutes 2-[2-(Fmoc-amino)ethoxy ethylamine hydrochloride (257 mg, 0.7083 mMol) was added to the stirring reaction mixture and left to react for 22.5 hours. LCMS analysis revealed the presence of the product in the reaction mixture. The reaction mixture was concentrated in vacuo and successively diluted in ethyl acetate and washed with an aq hydrochloric acid solution (1M). The collected organic layers were dried over magnesium sulphate, filtered and concentrated in vacuo to give a residue which was purified by flash column chromatography (chloroform to chloroform:methanol, 3%) to give the Fmoc derivative 4 (406 mg, 83%) as a white hygroscopic solid.

HRMS (TOF MS ES$^+$): found 1638.9775 [M+Na]$^+$ $C_{87}H_{133}N_{13}O_{16}Na$ requires 1638.9891.

Synthesis of the Cyclosporin—PEG-Amine Derivative (5)

To the FmoC protected CsA analogue 4 (97 mg, 0.06 mMol) was added piperidine (0.5 mL), and the reaction was stirred overnight at rt. The piperidine was removed on a rotary evaporator and the residue purified by chromatography using 5-10% MeOH containing 2% 880 ammonia in $CH_2Cl_2$. This gave the intermediate amine 5 (26 mg, 0.019 mMol, 31%) as yellow gum. This was used directly in the next step.

Synthesis of the Fluorescein—PEG-CsA Derivative (6)

To the amine 5 (22 mg, 18.6 mMol), 5-carboxyfluorescein (7 mg, 0.0187 mMol) and PyBOP (10 mg, 19 mMol) in $CH_2Cl_2$ (1 mL) was added diisopropylethylamine (9 mg, 13 µL, 76 mMol) and the reaction stirred overnight. The volatiles were removed on the rotary evaporator and the residue purified using reverse phase chromatography, C, 18, 5% MeOH to 95% MeOH in water. This gave the product 6 (10 mg, 0.0057 mMol, 48%).

LCMS (ES+) 1775 (M+Na$^+$), 1752 (M+H$^+$).

Example 2—Neuroprotective Properties of Compound 1

Induction of relapsing-progressive experimental autoimmune encephalomyelitis (EAE) was achieved as reported in Al-Izki et al. 2014, Brain, 137(Pt 1):92-108.

ABH mice were injected with 1 mg mouse spinal cord homogenate in Freund's adjuvant on days 0 and 7 post-induction to induce EAE and this was repeated on day 28 post-induction to induce a relapse. Animals were injected daily intraperitoneally with either vehicle [ethanol cremophor:phosphate buffered saline (1:1:18)] or 1 mg/kg Compound 1 on day 33 shortly before the anticipated onset of signs of relapse.

Animals were monitored for the development of clinical disease and the results in FIG. 1 represent the mean daily clinical score after induction of relapse. These results demonstrate that Compound 1 inhibits the accumulation of neurological deficit following onset of signs during EAE.

Example 3—Assessment of Toxicity of Cyclosporin Conjugates

A series of experiments were conducted to assess the toxicity of (a) unmodified cyclosporin A (CsA), (b) cyclosporin conjugated to a quinolinium moiety [Compound 1], and (c) cyclosporin conjugated to a flupirtine moiety [Reference Compound 1].

HepG2 cells were plated on 96-well tissue culture treated black walled clear bottomed polystyrene plates, 100 µL, (3000 cells) per well. After 24 hours the cells were dosed with the test compounds at a range of concentrations. At the end of the incubation period, the cells were loaded with the relevant dye/antibody for each cell health markers set out below. The plates were then scanned using an automated fluorescent cellular imager [ArrayScan VTI (Thermo Scientific Cellomics)].

The following cell health markers were measured:
a. Cell count—a decreasing number of cells per well indicates toxicity due to necrosis, apoptosis or a reduction in cellular proliferation.
b. Nuclear area—an increase in nuclear size indicates necrosis or G2 cell cycle arrest and a decrease indicates apoptosis.
c. DNA structure—an increase in DNA structure indicates chromosomal instability and DNA fragmentation.
d. Cell membrane permeability—an increase in cell membrane permeability is a general indicator of cell death.
e. Mitochondrial mass—a decrease in mitochondrial mass indicates loss of total mitochondria and an increase implies mitochondrial swelling or an adaptive response to cellular energy demands.
f. Mitochondrial membrane potential ($\Delta\Psi m$)—a decrease indicates a loss of mitochondrial membrane potential and mitochondrial toxicity, as well as a potential role in apoptosis signalling; an increase in mitochondrial membrane potential indicates an adaptive response to cellular energy demands.
g. Cytochrome c release—an increase in cytochrome c release is one of the hallmarks of the apoptosis signalling cascade.

Figure 2:
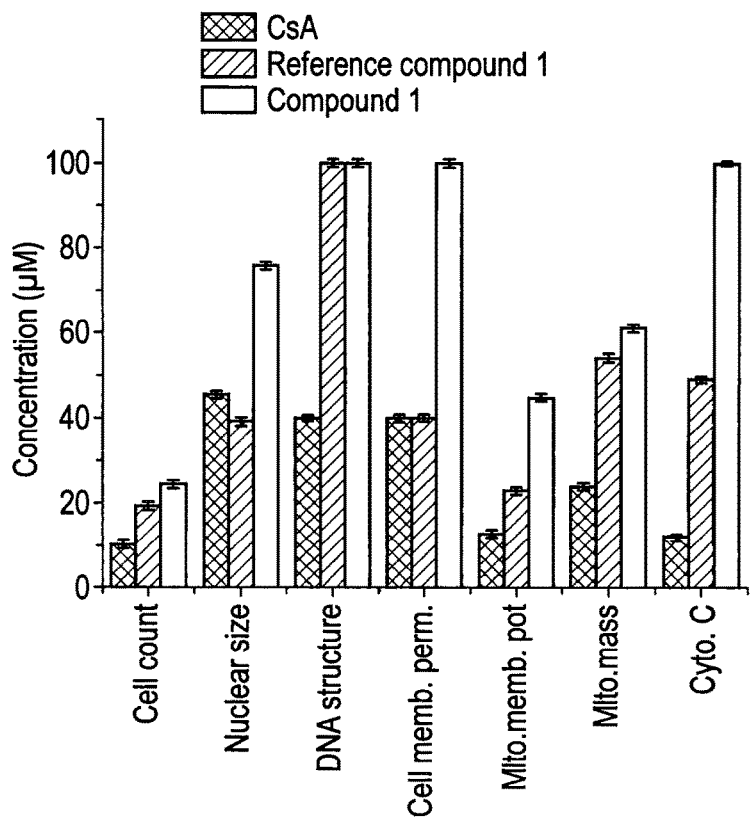
FIG. 2 shows the results from Example 3, in which a series of experiments were conducted to assess the toxicity of (a) unmodified cyclosporin A (CsA), (b) cyclosporin conjugated to a quinolinium moiety [Compound 1], and (c) cyclosporin conjugated to a flupirtine moiety [Reference Compound 1]. 100% in FIG. 2 represents no effect in the assay. These results show that conjugation of a quinolinium moiety to cyclosporin significantly reduced the toxicity of cyclosporin. A similar reduction in toxicity was not observed when cyclosporin in conjugated to other mitochondrial targeting groups, such as flupirtine.

The results are set out FIG. 2, in which 100% represents no effect in the assay. These results show that conjugation of a quinolinium moiety to cyclosporin significantly reduces the toxicity of cyclosporin. A similar reduction in toxicity is not observed when cyclosporin in conjugated to other mitochondrial targeting groups, such as flupirtine.

Example 4—Inhibition of $Ca^{2+}$ Mediated PT Pore Formation

In order to assess the efficiency of compounds on $Ca^{2+}$ mediated PT pore formation we measured calcium retention capacity (CRC) of isolated mouse liver mitochondria. The $Ca^{2+}$ concentration in the extra-mitochondrial solution was measured using the membrane impermeable low affinity fluorescent $Ca^{2+}$ sensitive dye Fluo-5N following repeated addition of $Ca^{2+}$ boluses (10 µM). Energised mitochondria take up $Ca^{2+}$, resulting in a declining fluorescent signal following the $Ca^{2+}$ bolus induced peak. Mitochondria take up and buffer $Ca^{2+}$ up to a threshold when intramitochondrial $[Ca^{2+}]$ reaches threshold to induce PT. This results in loss of mitochondrial membrane potential preventing further $Ca^{2+}$ uptake, resulting in lack of $Ca^{2+}$ buffering, represented by stepwise increase in extramitochondrial $[Ca^{2+}]$ at each $Ca^{2+}$ addition. The amount of $Ca^{2+}$ required to induce PT characterizes its $Ca^{2+}$ sensitivity and defines mitochondrial CRC. Inhibition of CypD, the $Ca^{2+}$ sensor of PT, thus leads to increased CRC.

Figure 3:
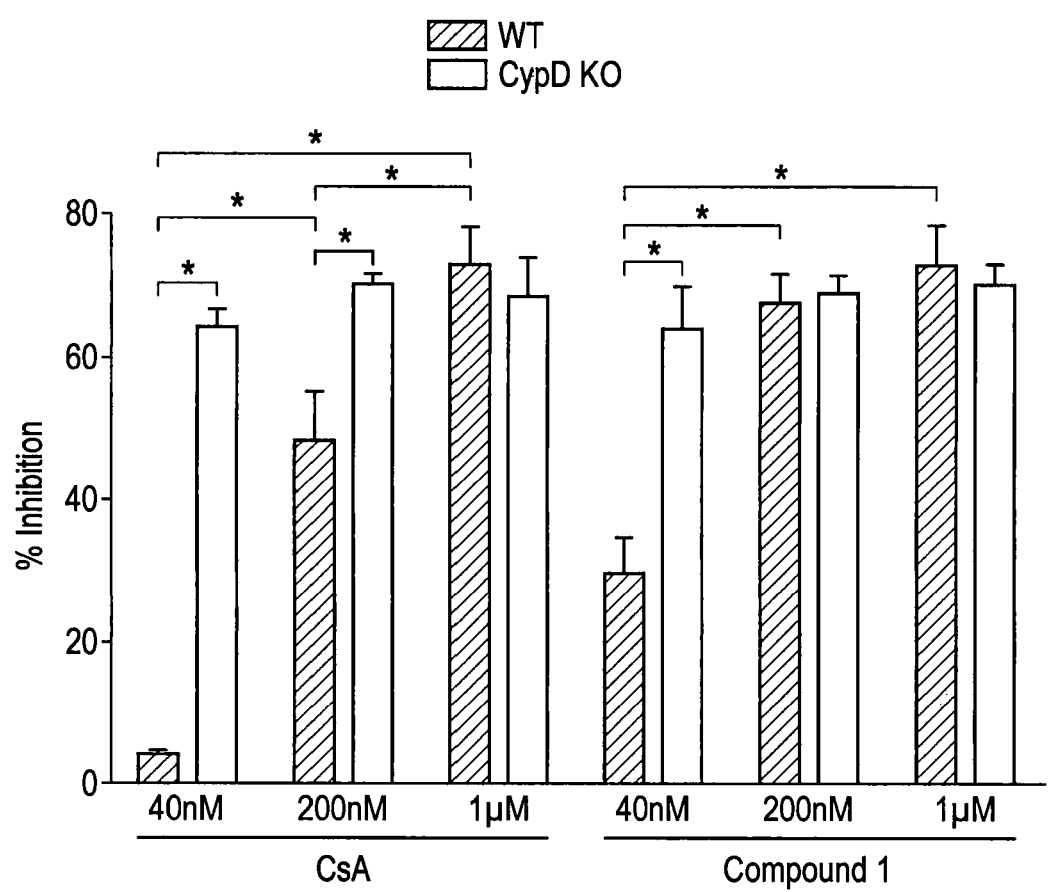
FIG. 3 shows quantification of the dose dependent effects of CsA and Compound 1 on CRC (PT) in liver mitochondria isolated from WT and CypD KO animals, as described in Example 4. Percentage inhibition denotes increase in CRC compared to DMSO treatment, normalised to WT. * $p<0.05$ (t-test)

Compound 1 inhibited $Ca^{2+}$-induced PT (i.e. increased CRC) with significantly higher potency as compared to CsA and the non-immunosuppressive inhibitor SmBzCsA. Compound 1 showed half-maximal inhibition at ~10 nM as compared to ~40 nM for CsA in the CRC assay. These results show that Compound 1 is approximately a four-fold more potent inhibitor of $Ca^{2+}$ mediated PT pore opening than CsA. In order to confirm that Compound 1 selectively targets CypD to reduce $Ca^{2+}$ sensitivity of PTP formation, the efficiency of the compound was tested on mitochondria isolated from CypD knockout mice. Neither CsA nor Compound 1 had any effect on CRC from CypD KO mice (see FIG. 3), whereas CRC in the mitochondria from WT mice was significantly increased by both compounds, proving that Compound 1 inhibits PT pore opening via binding to CypD.

Example 5—Effects on Mitochondrial Membrane Potential or Oxidative Phosphorylation To assess the potential adverse effects of compounds, we measured fundamental mitochondrial functional parameters both in DIV 8-9 rat cultured neurons and in isolated mitochondria, and compared the effects of CsA and Compound 1 above concentrations causing maximal inhibition of the PT pore (>200 and 40 nM, respectively).

Figure 4A:
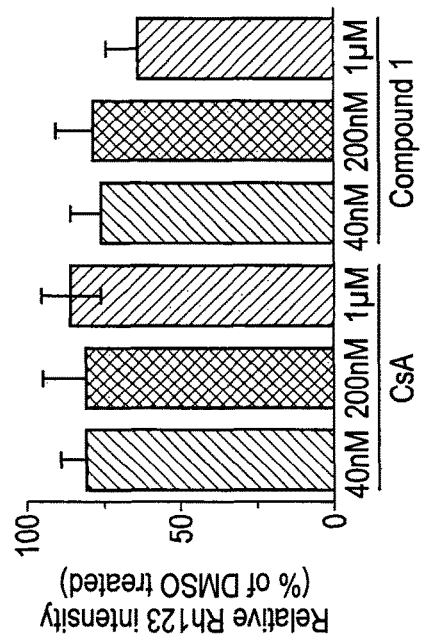
FIGS. 4A to 4F relate to the assessment of mitochondrial toxicity in Example 5. Mitochondrial parameters were measured in DIV 8-9 rat cortical neurons (A, E) and isolated rat liver mitochondria (B-D, F). A, B: Mitochondrial membrane potential was measured in tetramethyl-rhodamine methylesther (TMRM) loaded neurons using ImageXpress MicroXL in (A) and rhodamine-123 loaded isolated mitochondria using a fluorescent plate reader in (B). Values in are normalised to DMSO (100%) and FCCP (2 M, 0%) treated samples. * $p<0.05$ (one way ANOVA) C, D: $O_2$ consumption was measured in mitochondria isolated from rat liver in the presence of glutamate and malate using Oroboros high resolution oxygraph. The effect of compounds on basal, leak (oligomycin, 2.5 μM) and maximal uncoupled respiration (FCCP, titrated to give maximum effect) is shown, as compared to basal, DMSO controls. * $p<0.05$ (paired t-tests). E, F: ATP levels in cortical neurons (E) and ATP production of isolated mitochondria in the presence of substrates and ADP (F) was measured using a luciferase assay. Iodoacetic acid (IAA, 1 mM) and oligomycin (oligo, 2.5 μM) was used to show the contribution of glycolysis and mitochondrial ATP synthesis, respectively. * $p<0.05$ (t-test).
Figure 4B:
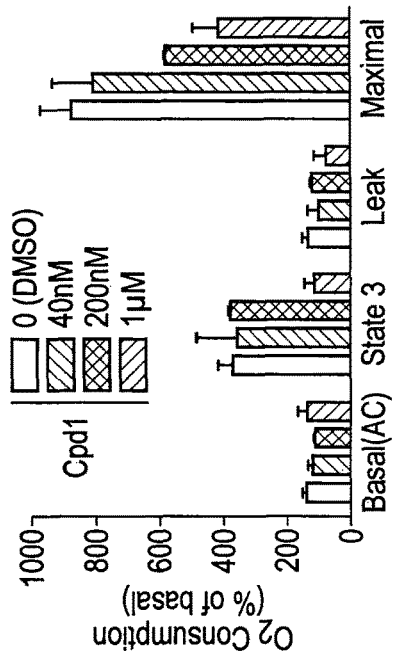
Figure 4C:
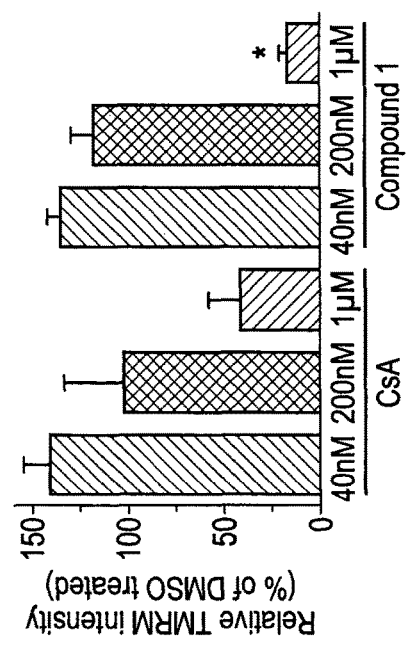
Figure 4D:
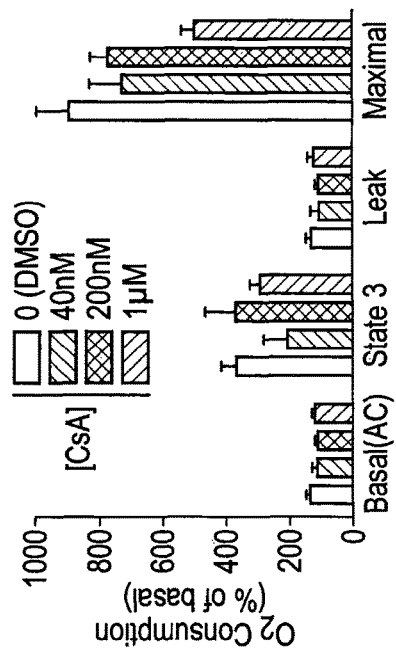
Figure 4F:
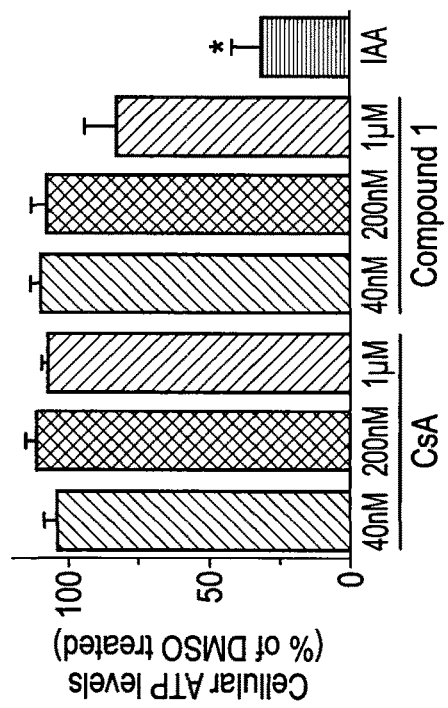
Figure 4E:
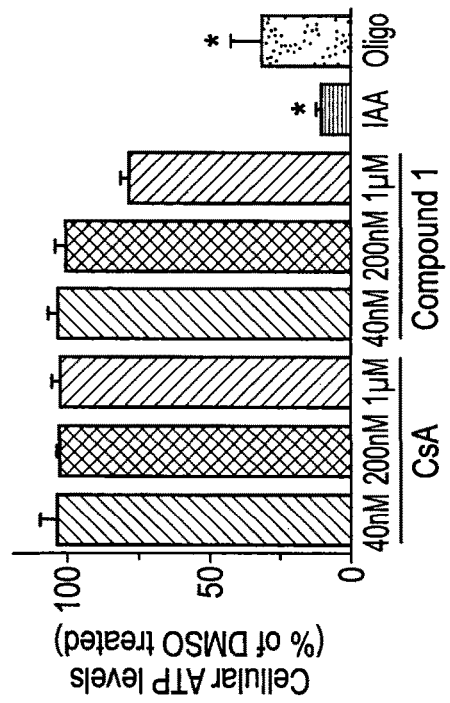

Neither mitochondrial membrane potential (FIG. 4A,B), oxygen consumption (FIG. 4C, D) and ATP production (FIG. 4E, F) were affected by supramaximal Compound 1 (up to 200 nM) or CsA (up to 1 µM) in either models. Compound 1 inhibited neuronal mitochondrial membrane potential only at ~25 times higher concentrations (1 µM), as compared to that of its maximal inhibitory effect (40 nM) on the PT pore.

Figure 5A:
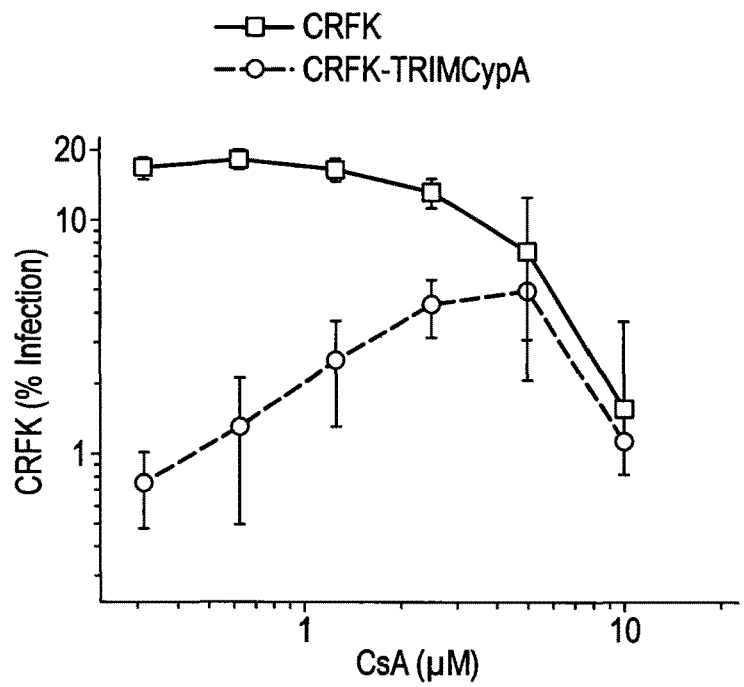
FIGS. 5A and 5B shows the assessment of in cell CypA binding as described in Example 6. CRFK cells transduced with either empty vector (filled squares) or TRIM-CypA (open circles) were infected with VSV-pseudotyped GFP-expressing HIV-1 vector, in the presence of DMSO or increasing concentration of drug. A CsA, B. Compound 1. Viral infection was measured by flow cytometry at 48 hr post infection. Data are the average of three independent experiments.
Figure 5B:
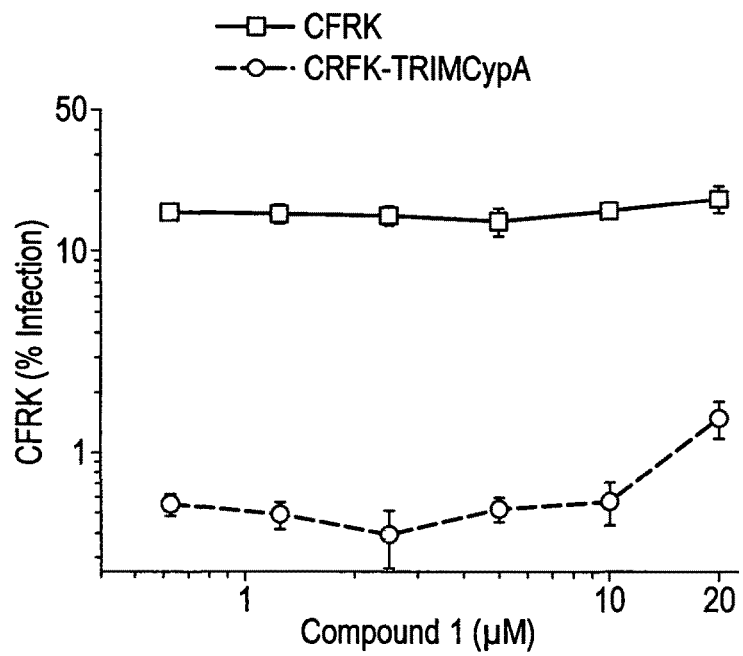
Figure 6A:
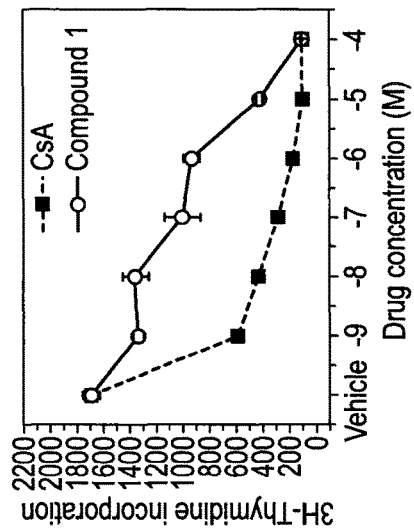
FIGS. 6A to 6D show the results from Example 8, and that Compound 1 exhibits less immunosuppressive activity than CsA. Mitogenesis in vitro, $4 \times 10^{-5}$ cells normal mouse splenocytes were incubated with A 5 μg/ml concanavalin A B Mitogenic CD3/CD28 monoclonal antibodies or C splenocytes from MOG residues 35-55 peptide immunized mice in the presence of 5 μg/ml MOG peptide with vehicle or compounds for A, B 2 or 4 C days prior to the addition of 1 μCi $^3$H-thymidine and were harvested 16-20 h later and tritiated thymidine incorporation was assessed by beta scintillation counting. The results represent the mean±SEM of triplicate samples. D Low doses of Compound 1 in vivo exhibited no immunosuppressive activity. 25 μl of 2.5% Oxazolone (OX) or acetone:olive oil (4:1) vehicle (AOO) was applied to the ear skin of ABH mice on day 0. On day 3 the draining auricular lymph nodes of 3-4 mice/group were removed and $5 \times 10^5$ cells were cultured overnight in the presence of 1 μCi $^3$H-thymidine. Animals were treated with 0.1 ml vehicle or 0.1-10 mg/kg Compound 1 or 50 mg/kg CsA. The results represent the mean±SEM of at least quadruplicate samples.
Figure 6B:
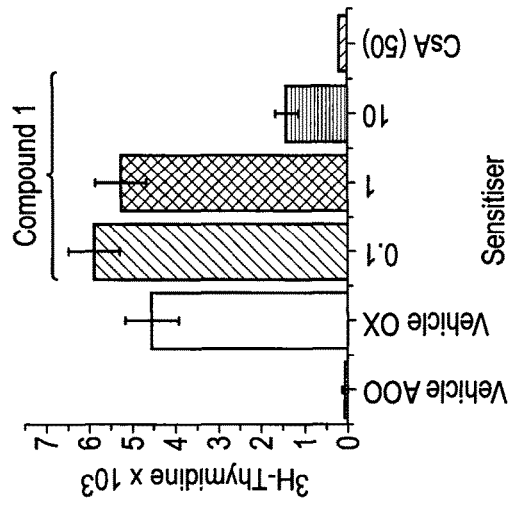
Figure 6C:
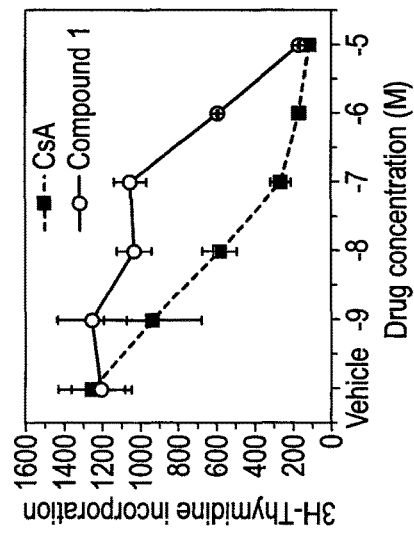
Figure 6D:
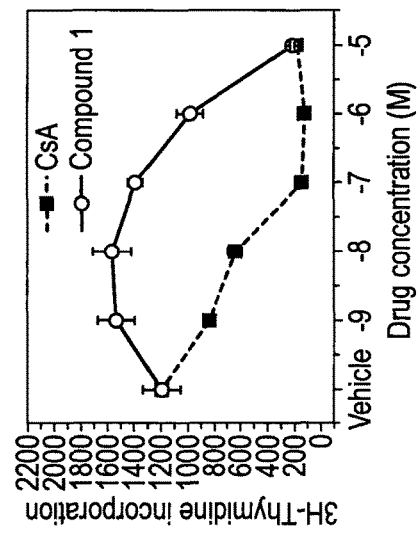

Example 6—Estimation of Cellular CypA Activity Using an HIV Based Cellular Assay To test cellular cyclophilin selectivity of compounds of the invention we conducted a human immunodeficiency virus (HIV-1) based cellular assay responsive to CypA inhibition. HIV-1 infection of cell lines can be inhibited by the expression of an artificial antiviral protein, comprising the RBCC domains of owl monkey tripartite motif-containing protein 5 (TRIM5) fused to human CypA (TRIM-CypA). TRIM-CypA inhibited viral infection by 32 fold in the absence of drug (FIG. 5A). CsA rescued infectivity through CypA inhibition whereas Compound 1 rescued infectivity poorly and only at concentrations >10 µM (FIG. 5B). A drop to infectivity in non-restricting cells was due to drug toxicity at 5 µM CsA and above. Compound 1 showed no evidence for toxicity at any of the concentrations tested.

Example 7—Pharmacokinetics

The pharmacokinetics of Compound 1 were determined in normal ABH mice at 10 mg/kg i.p. at 2 and 4 h. The results are set out below in Table 2.

TABLE 2

| Time (hours) | Plasma | | Brain | |
|---|---|---|---|---|
| | µg/mL | µM | µg/mL | nM |
| 2 | 13.74 ± 3.84 | 10.1 | 0.018 ± 0.0019 | 13.2 |
| 4 | 4.90 ± 0.85 | 3.60 | 0.017 ± 0.0016 | 12.5 |

Compound 1 showed high plasma levels of 10.1 µM at 2 h and appreciable brain levels (13.2 nM). This is broadly comparable with CsA in rodents (Schinkel et al, 1995.

Example 8—Immunosuppressive Properties

The inhibitory effect of Compound 1 on T cell responses was examined in vitro. Concanavalin A and mitogenic CD3/CD28 monoclonal antibodies induce T cell proliferative responses that were inhibited by CsA typically in the 1-10 nM range (FIG. 6 panels A to C). Compound 1 only exhibited marked immunomodulation in the 1-10 µM range and was cytopathic at 100 µM. Similarly, Compound 1 exhibited markedly less immunosuppressive activity compared to CsA in myelin peptide (myelin oligoglycoprotein residues 35-55) antigen-induced T cell proliferation.

To identify non-immunosuppressive doses of potential neuroprotective compounds for use in models of MS (Al-Izki et al, 2014) we employed a model using epicutaneous application of the ear skin sensitizer, oxazolone, to induce a T cell proliferative response in the draining auricular lymph node peaking 3 days later (Baker et al, 2011). Dose-response of Compound 1 in this contact hypersensitivity model showed: daily injection of 1 mg/kg and 0.1 mg/kg i.p. had no effect while 10 mg/kg i.p. inhibited the T cell response. CsA was immunosuppressive (FIG. 6D) at doses known to inhibit T cell proliferation and EAE (O'Neill et al, 1992). Daily dosing of 1 mg/kg i.p. Compound 1 was therefore chosen as a non-immunosuppressive dose for in vivo studies.

Example 9—Further Investigations into the Neuroprotective Properties of Compound 1

Figure 7A:
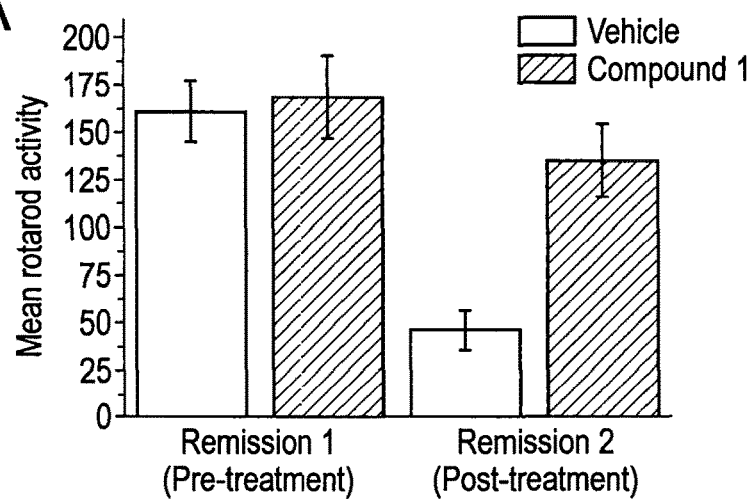
FIG. 7A shows the mean rotarod activity representing the mean±SEM time before falling/failing to stay on an accelerating rotarod before (on day 27) or after (on day 45) treatment with either vehicle (white bar) or Compound 1 (grey bar). * $P<0.001$ compared to vehicle treatment.
Figure 7B:
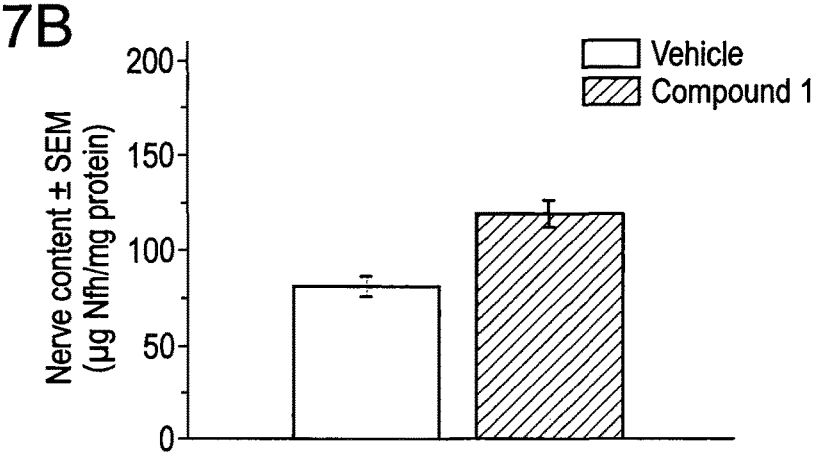
FIG. 7 shows the results from Example 9.
Figure 7C:
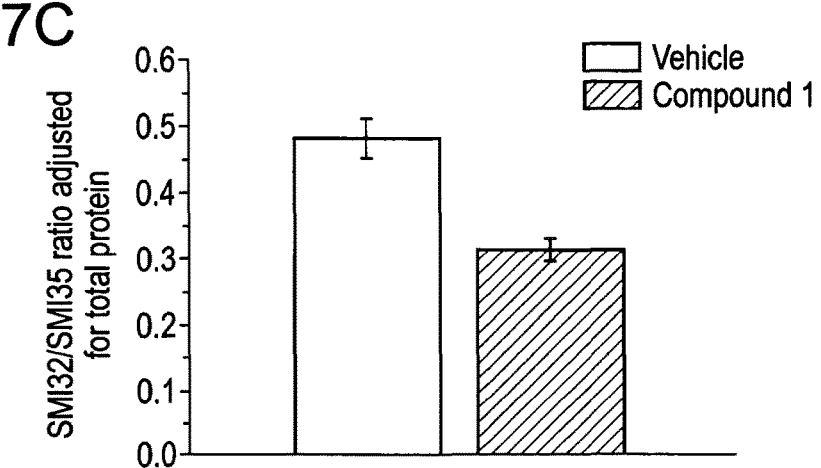

To support the results discussed above in Example 2, further studies were carried out which supported the conclusions from Example 2. Specifically, the outcome was supported by objective rotarod activity outcomes (FIG. 7A). Animals exhibited comparable rotorod activity on day 27 during the first remission (168.8±21.8 s Compound 1 vs. 161.1±16.0 s vehicle) but there was significantly (P<0.001) less loss of motor co-ordination following treatment with Compound 1 (FIG. 7A). During the second remission after relapse Compound 1-treated animals maintained activity on an accelerating rotorod for 135.0±42.9 s compared to only 46.3±10.1 s in vehicle treated animals. This activity strongly correlates with spinal nerve content in this assay (Al-Izki et al, 2012b) and it was found that Compound 1 treated animals lost significantly (P<0.01) less nerves (FIG. 7B) and axons (FIG. 7C) within the spinal cord than vehicle treated animals. Thus Compound 1 exhibits neuroprotective potential and can inhibit loss of nerves due to the inflammatory penumbra during EAE.

Figure 8A:
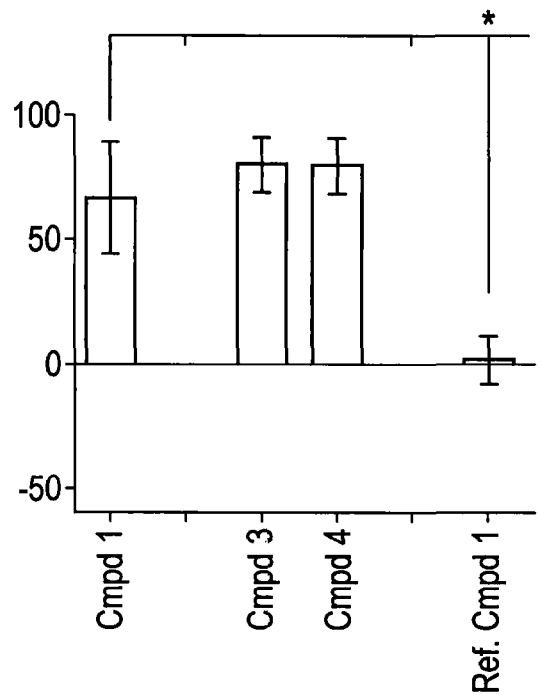
FIG. 8A shows when a concentration of 40 nM was used.
Figure 8B:
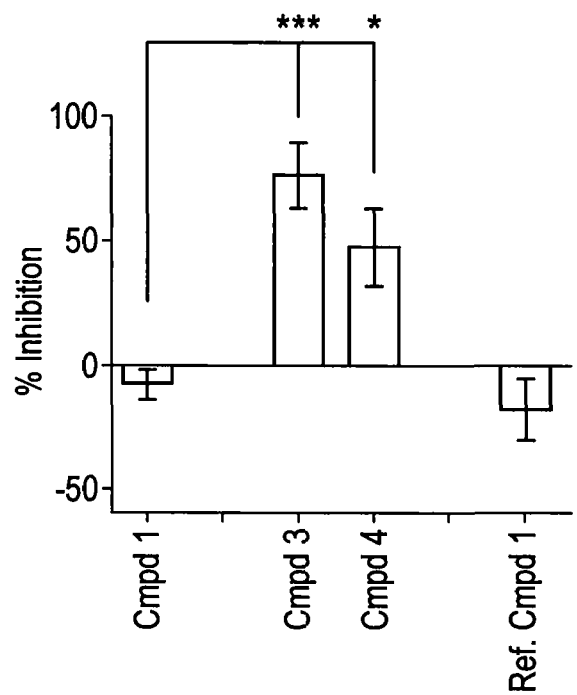
FIG. 8B shows the results when a concentration of 8 nM was used.

Example 10—Further Investigations into Inhibition of $Ca^{2+}$ Mediated PT Pore Formation Further experiments were carried out using the techniques discussed in Example 4. In particular, the inhibition of $Ca^{2+}$ mediated PT pore formation was determined for Compounds 1, 3 and 4 and Reference Compound 1 at two different concentrations (40 nM and 8 nM). The results at 40 nM are depicted in FIG. 8A. The results at 8 nM are depicted in FIG. 8B.

As is evident from FIG. 8A, at the 40 nM concentration, Compounds 1, 3 and 4 show similar levels of inhibition of $Ca^{2+}$ mediated PT pore formation. When the concentration of test compound is reduced to 8 nM, Compounds 3 and 4 retain high levels inhibition of $Ca^{2+}$ mediated PT pore formation, whilst Compound 1 shows negligible inhibition at this concentration.

Biological Methods

Mitochondrial Isolation

Subcellular fractionation was performed as previously described (Astin et al, 2013). Briefly, C57BL/6J WT or cypD (Lim et al, 2011) −/− male mice of 3-6 months were sacrificed by cervical dislocation, and their liver was removed and placed immediately into ice-cold isolation buffer (250 mM mannitol, 5 mM HEPES, 0.5 mM EGTA, pH 7.4). At 4° C., the liver was rinsed in PBS to remove excess blood, and any fat and connective tissue was eliminated. PBS was then replaced with isolation buffer containing 1 mM PMSF, and the liver was chopped into pieces (approximately 2 mm in length). Tissue was then homogenized in this solution until no solid matter remained, and then centrifuged at 800G for 10 minutes at 4° C. The nuclear pellet was then discarded, and the post nuclear supernatant retained, and centrifuged at 10300G for another 10 minutes at 4° C. The postmitochondrial supernatant was discarded, and the mitochondrial pellet was resuspended in isolation buffer and PMSF, and kept on ice. Protein levels were quantified using a ThermoScientific BCA protein quantification assay, as per manufacturer's instructions.

Calcium Retention Capacity Assay

Isolated mitochondria were resuspended (500 μg protein/ml) in MSK buffer (75 mM mannitol, 25 mM sucrose, 5 mM potassium phosphate monobasic, 20 mM Tris-HCl, 100 mM KCl, and 0.1% bovine serum albumin, pH 7.4) supplemented with 10 mM succinate, 1 μM rotenone and 1 μM Fluo5N. 200 μl mitochondrial suspension per well was used in 96 well microplates. Compounds were incubated for ten minutes before the plate was assayed in a Fluostar Optima plate reader, using Ex/Em filters at 480/520 nM; $CaCl_2$ was injected approximately every 6.5 minutes for 80 minutes (12 total injections, final concentration of 75 μM). To calculate % inhibition of $Ca^{2+}$ induced pore opening, first areas under each curve were calculated, and controls without $CaCl_2$ addition were subtracted as background. The background corrected values were then expressed as the fraction of controls without mitochondria, representing the total amount of $Ca^{2+}$ added, unbuffered by mitochondria. Percentage inhibition for each [compound] was then calculated as the % of the corresponding value for the untreated condition. Significance was assessed by one way ANOVA, in comparison to CsA control. For experiments with CypD −/− mice, 100 ul mitochondrial suspension per well was used. $CaCl_2$) was injected approximately every 6.5 minutes for 135 minutes (20 total injections, final concentration of 266 μM). Data were background corrected and expressed as the fraction of controls without mitochondria, and then normalised to the wild type no drug condition. Significance was assessed by one way ANOVA.

Respirometry

Oxygen consumption was measured using Oroboros Oxygraph-2K as previously described (Astin et al, 2013). Prior to the assay, the Oxygraph chambers were calibrated with Miro5 buffer (0.5 mM EGTA, 3 mM $MgCl_2.6H_2O$, 60 mM K-lactobionate, 20 mM taurine, 10 mM $KH_2PO_4$, 20 mM HEPES, 110 mM sucrose, 1 g/l BSA (essentially fatty acid free)). Isolated mitochondria were suspended in Miro5 (at 100-200 μg/ml), loaded into the chamber together with substrates (malate, 2 mM; glutamate, 10 mM), and the $O_2$ flow signal was allowed to stabilise to the basal respiration rate (approx. 10 min). Compounds were added to the chambers at the following concentrations and order: DMSO/CsA/Compound 1 (concentration as indicated) to produce basal rate after compound (basal AC), ADP (2.5 mM) to give state 3 respiration, oligomycin (2.5 μM) to give leak respiration, FCCP (titrated to produce maximal respiratory capacity), and antimycin A (2.5 μM) to give non-mitochondrial respiration.

Measurement of Mitochondrial Membrane Potential

DIV 8-9 rat cortical neurons were incubated for 40 minutes at 37 C with the cell permeant cationic dye tetramethylrhodamine methyl ester (TMRM, 25 nM), and fluorescence was measured using the ImageXpress Micro XL system (Molecular Devices). Fluorescence was measured for 7 minutes prior to addition of DMSO, CsA or Compound 1 (both at 40 nM and 1 μM), and then for a further 50 minutes before the addition of the mitochondrial uncoupler carbonyl cyanide-4-(trifluoromethoxy)phenylhydrazone (FCCP, 5 μM) as a positive control. The minimum value after the addition of compound (prior to the addition of FCCP) was taken, and this was expressed as a % (using baseline as 100% and FCCP as 0%), and then normalized to DMSO (100%). Significance was assessed by one-way ANOVA, in comparison to DMSO control.

Measurement of Mitochondrial Membrane Potential (Ex Vivo)

Freshly isolated mouse liver mitochondria were suspended in MSK buffer containing 10 ug/ml rhodamine123 (dequench mode), at a concentration of 500 ug/ml, and plated in an opaque black 96 well plate. Baseline fluorescence was then measured every 60 seconds for 5 minutes in a Fluostar Optima (Ex480/Em520) before manual addition of compounds (concentrations as specified). Fluorescence measurements were continued for 45 minutes until the addition of 2 uM FCCP, followed by a further 10 minutes of fluorescence readings.

ATP Production

Freshly isolated mitochondria were resuspended in MSK buffer (containing 10 mM glutamate and 2 mM malate) at 1 mg/ml and plated in opaque white 96 well plates, or for neuronal assays, neurons were used 9 days after plating at 15000 cells/well. Drugs were added at the concentrations specified, and for mitochondrial assays were incubated for ten minutes before addition of ADP (5 mM), followed by another 45 minutes. For neuronal assays, drugs were added in neurobasal medium and incubated for 60 minutes. Cell Titer Glo reagent was then added, and the plate shaken for 2 minutes in the dark to lyse cells/mitochondria and release ATP. The plates were incubated a further ten minutes and then luminescence values read using an Optima FluoStar.

High Content Screening

HepG2 cells were seeded in black, clear-bottom 96-well tissue culture plates at a density of 3000 cells per well. The cells were incubated for 24 h in culture medium and then exposed (in three replicates) to increasing doses of test compound or to vehicle control (0.5% DMSO). The cells were exposed for 72 h before running the high content screening (HCS) assays. The HCS assay was multiplexed to determine mitochondrial membrane potential and mitochondrial mass using MitoTracker® (Life Technologies), cytochrome C release (antibody, Abcam), membrane permeability, YO-PRO™-1 (Life Technologies). Cell count, nuclear size and DNA structure were also measured Hoechst 33342 (Life Technologies). Following staining of the HepG2 cells fluorescence was analyzed by image acquisition with a Thermo Fisher Cellomics® ArrayScanVTI High Content Screening Reader (ThermoFisher Scientific Inc., Waltham, Mass.) and vHCS™ view software (ThermoFisher Scientific Inc.). Twenty fields were imaged per well using a 10× wide field objective. The image acquisition data were normalized to vehicle control values. Dose-response curves were defined and evaluated with the following equations:

$$\xi(C; c; \omega) = (\ln(C) - c)/\omega; \tag{1}$$

$$t(\xi) = (1 + \tan h(\xi))/2; \tag{2}$$

$$R(t; R0; R\infty) = R0(1-t) + R\infty t; \tag{3}$$

In which C represents the test compound concentration and R0, R∞, c, and ω are fitting parameters. The final response at a given concentration C is expressed as R(t(ξ(C; c; ω));R0;R∞). It was restricted such that ω>0, which implies R→R0 as C→0 and R→R∞ as C→∞. The coefficient of determination ($R^2$) was calculated for each compound and dose-response curve. An $R^2$ value of greater than 0.65 was used as QC criteria and was required in all response curves Cell Based Assay for CypA Activity VSV-G pseudotyped GFP-encoding HIV-1 vector was prepared by triple plasmid transfection of 293T cells with Fugene 6 (Roche) as follows. Confluent 293T cells in a 10 cm dish were transfected with a mixture of 10 µl Fugene-6 in 200 µl OptiMEM (Gibco), with 1 µg of pMDG VSV-G expression vector (Naldini et al, 1996), 1 µg of p8.91 HIV-1 gag-pol expression vector (Zufferey et al, 1997), and 1.5 µg of lentiviral expression vector encoding enhanced GFP protein, CSGW (Bainbridge et al, 2001). Viral supernatant was collected 48 h post transfection and stored at −80° C.

To generate CRFK cells stably expressing N-terminally HA-tagged TRIM-CypA from an EXN-based vector, MLV vector was prepared as above, using pMDG, CMVi MLV gag-pol expression vector, and gammaretroviral expression vector encoding a fusion protein comprising human CypA downstream of owl monkey TRIM5 RBCC (EXN-TRIM-CypA) (Ylinen et al, 2010). CRFK cells, which are null for TRIM5α activity (McEwan et al, 2009) were then transduced with vector, followed by selection of cells in 1 mg/ml G418 (Invitrogen).

To test for the ability of drug to rescue HIV-1 infectivity in the presence of TRIM-CypA, CRFK cells were infected with a single dose of virus that infected around 20% of the cells, in the presence of DMSO, CsA (0.3-10 µM) or Compound 1 (0.6-20 µM). Infectivity was measured by flow cytometry, 48 hrs post infection.

In Vitro Mitogenic T Cell Stimulation

Spleens were isolated from ABH mice and tissue was homogenized through a cell strainer (BD Biosciences, Oxford, UK) into Dulbecco's modified eagle medium (DMEM; Invitrogen, Paisley, UK) containing 10% foetal calf serum (FCS, Gibco, Invitrogen), 2 mM L-glutamine (Invitrogen, UK), 100 U/ml penicillin and 100 µg/ml streptomycin (Invitrogen) and 50 µM 2-mercaptoethanol (Invitrogen). Cells were centrifuged at 500 g for 5 min and erythrocytes were lysed using 0.87% ammonium chloride following incubation for 5 min at 37° C. Cells were washed and viable cells counted using trypan blue (Sigma Aldrich, Poole, UK) exclusion. 4×10$^5$ cells/well were incubated 96 well microtest U-bottom plates (Falcon BD, Oxford UK) in final volume of 200 µl DMEM medium. Cells were incubated with either ten-fold dilutions (range 10 nM-10 µM) of CSA (Sandoz, Basel, CH) or Compound 1 diluted in DMEM medium from a 50 mM stock in dimethyl sulphoxide. Cells were incubated with either: 5 µg/ml concanavalin A (Con A. Sigma Aldrich) mitogen; 0.5 µg/ml mitogenic mouse CD3 and mouse CD28-specific antibodies (Pharmingen, Oxford, UK). The cells were incubated in 37° C. during 18-22 h, before addition of 1 µCi$^3$H-thymidine (PerkinElmer, Mass., USA) per well. After additional incubation in 16-20 h the 96-well plates (Microtest U-bottom, Falcon BD) were harvested (Harvester 96, Mach III M, TOMTEC) onto glass-fibre filters (PerkinElmer). After drying, a scintillation sheet (MeltiLexA; PerkinElmer) was melted onto the filter using a hot plate (RET Basic, IKA, Germany). Samples were analysed using scintillation counting (MicroBeta Plus, Liquid Scintillation Counter, PerkinElmer, WallacOy, Finland) and $^3$H-thymidine incorporation was assessed in at least triplicate samples.

Myelin Antigen-Induced T Cell Proliferation

ABH mice were injected subcutaneously in the flank with 100 µg myelin oligodendrocyte glycoprotein (MOG) peptide residues 35-55 (Cambridge Research Biochemicals Ltd, Billingham, UK) emulsified in Freunds adjuvant containing 200 µg *Mycobacterium tuberculosis* H37 RA (DifcoBacto, Mich., USA) on day 0 and 7 (Amor et al, 1994). Spleens were collected and prepared and analysed as above except that mitogens were replaced with 5 µg/ml MOG 35-55 peptide and cells were incubated for 72 h before addition of tritiated thymidine.

Pharmacokinetic Analysis

ABH mice (n=4) were injected intraperitoneally with 0.1 ml of either 10 mg/kg Compound 1. Animals were killed 2 h and 4 h later with CO$_2$ overdose and blood was immediately collected from the heart following death and added to Microtainer (BD, Oxford, UK) tubes, centrifuged using an Eppindorf microfuge and plasma collected. Following the remove of blood the brain was rapidly (<30 s) dissected from the skull and stored at −80° C. prior to analysis by a Contract research Organisation (CRO) using liquid crystal mass spectroscopy.

In Vivo T Cell Proliferation

The contact sensitiser 4-ethoxymethylene-2-phenyl-2-oxazolin-5-one (oxazolone, OX, Sigma) was dissolved (25 mg/ml) in 4:1 acetone:olive oil (AOO). Mice (n=3 per group) received epicutaneous application of either 25 µl of 2.5% OX or AOO on the dorsum of the ear on day 0 (O'Neill et al, 1992). The draining auricular lymph nodes were removed three days later and the induced proliferative response was assessed as previously described. Briefly, 5×10$^5$ cells per well were cultured in RPMI-1640 medium with glutamate (Gibco®, Invitrogen Ltd, Paisley UK), supplemented with 0.5 mM sodium, in round-bottomed 96 well plates overnight at 37° C. in a humidified atmosphere of 5% CO$_2$. In the presence of 1 µCi$^3$H-thymidine (PerkinElmer, Mass., USA) per well. DNA synthesis was estimated using beta scintillation counting as above Animals received daily i.p. injections of either vehicle or Compound 1 from day zero to three (O'Neill et al, 1992); (Al-Izki et al, 2012a). Results are expressed as mean±SEM thymidine incorporation counts per minute (CPM)

Induction of Relapsing-Progressive EAE

Mice were injected subcutaneously (s.c.) with 1 mg freeze-dried mouse spinal cord homogenate (SCH) in Freunds adjuvant on day zero and seven as described previously (Al-Izki et al, 2012a). After the initial paralytic disease and subsequent remission, a relapse was induced by a further injection of SCH in Freunds incomplete adjuvant on day 28 to induce a relapse 7 days later (Al-Izki et al, 2012a). Studies were randomised, blinded and powered as described previously (Al-Izki et al, 2012a). Neurological scores were graded as 0=normal; 1=limp tail, 2=impaired righting reflex, 3=hindlimb paresis, 4=complete hindlimb paralysis, and 5=moribund/death (Al-Izki et al, 2012a). Results are expressed as mean±SEM maximum or minimum neurological score and mean day of onset±SD. Differences between groups were assessed using Mann Whitney U statistics (Al-Izki et al, 2012a). Motor control and co-ordination was assessed on an accelerating (4-40 rpm, accelerating at 6 rpm/25 s) RotaRod (ENV-575M, Med Associates Inc, St. Albans, Vt., USA) as described previously (Al-Izki et al, 2012a). This was performed one day before induction of relapse and at the termination of the experiment on day 45. RotaRod assessment was performed blinded to treatment. Animals were randomised to vehicle or treatment based on their RotaRod scores. Results are expressed as mean±SEM time that animals maintained rotarod activity. Differences between groups were assessed using Students t test, incorporating a test for equality of variance and normality (Al-Izki et al, 2012a). At the end of the experiment the spinal cord was removed and an enzyme linked immunosorbent assay (ELISA) for heavy chain neurofilament on spinal cord was performed and total nerve content of each spinal cord was estimated following calibration against neurofilament protein standards as described previously (Jackson et al, 2005); (Al-Izki et al, 2012a).

Neurofilament ELISA

Neurofilament level as a correlate of spinal cord axonal content was determined as followed. Spinal cords were collected from the spinal columns of untreated (n=11) and Compound 11 mg/kg treated (n=13) animals at the second remission phase of disease post relapse at day 45 post disease induction. Tissues snap frozen and stored at −80° C. prior to homogenisation. Tissues were homogenised in a glass homogeniser in 1 ml/100 mg of spinal cord tissue wet weight homogenisation buffer (0.2 mM PMSF, 1 mM EDTA, 1 mM EGTA, 4M Urea, 10 mM Tris-HCl Sigma UK, pH 7.2,) plus 1:100 HALT protease inhibitor cocktail (Thermo Fisher, UK) and further homogenised by sonication twice for 10 seconds (Cole-Parmer Instruments, USA). Samples were spun down at 13,000 rpm in a bench top centrifuge (Eppendorf, UK) and the supernatant was collected and stored at −80° C. prior to neurofilament determination. Samples were thawed on ice and an enzyme linked immunosorbent assay for heavy chain neurofilament was performed. Briefly, a 96 well plate was coated overnight at 4° C. with capture antibody (1:5000 SMI-35 anti-neurofilament H. Covance Inc. Cambridge Bioscience, Cambridge, UK) in coating buffer (0.15M $Na_2CO_3$, 0.35M $NaHCO_3$, Sigma, UK, pH 9.6. Following one wash in wash buffer (150 mM NaCl, 10 mM Tris-HCl, 0.1% Tween 20, Sigma, UK pH 7.5), non-specific binding was blocked by incubation with 5% bovine serum albumin (Sigma, UK) in wash buffer for 1 hour at room temperature. Following a wash step, samples and standards (Porcine neurofilament heavy chain, Chemicon International, UK) were diluted in wash buffer with 1% bovine serum albumin and incubated on the plate for 1 hour at room temperature. Following 5 wash steps, the detector antibody was applied (1:1000 rabbit anti-NF200, Sigma, UK) and incubated for a further hour at room temperature. The plate was washed 5 times and the reporter antibody was applied (1:1000 swine anti-rabbit HRP conjugate, DAKO, UK). Following a final 5 washes, tetramethylbenzidine substrate (Sigma, UK) was applied and colour production measured on a BioTek Synergy HT (USA) plate reader at 450 nm.

The protein content of the samples was determined by micro-BCA assay (Pierce, Thermo Fisher, UK and axonal neurofilament levels in each were calculated as µg neurofilament per mg of total protein in each sample.

SMI32/SMI35 Ratio

A 96 well plate was coated with either SMI35 anti-phosphorylated Nf-H or SMI32 anti-non-phosphorylated Nf-H which is a marker of axonal damage/dystrophy (Covance Inc. Cambridge Bioscience, Cambridge, UK) antibodies at 1;5000 dilution as above. Due to the nature of the epitope, an absolute standard for SMI32 reactive neurofilaments was unavailable. Nf-H$^{SMI32}$ was therefore presented as a proportion of total neurofilament as measured by absorbance level and corrected for total protein levels in each sample.

Statistics

The clinical scores are presented as the mean daily neurological score±standard error of the mean (SEM). Differences in clinical scores were assessed using non-parametric, Mann Whitney U statistics. Differences in rota activity; and quantitative neurofilament ELISA was assessed using a students t test incorporating tests for equality of variance using Sigmaplot (Systat Software, Inc., San Jose, USA) (Al-Izki et al, 2012a). Calcium retention assay: Data were background corrected and expressed as the fraction of controls without mitochondria, and then normalised to the wild type no drug condition. Significance was assessed by one way ANOVA.

Respirometry: Data were analysed by subtracting the antimycin A respiration rate to give mitochondrial specific $O_2$ flow, and were then expressed as a percentage of the basal $O_2$ flow. Significance was assessed by one way ANOVA, in comparison to DMSO control.

Mitochondrial membrane potential measurements: Data were normalized, using the baseline as 100% and the FCCP value as 0% and normalized to DMSO. Significance was assessed by one-way ANOVA, in comparison to DMSO control.

ATP production: Data were normalised to DMSO control, and significance assessed by one way ANOVA.

LIST OF REFERENCES

Al-Izki S, Pryce, O'Neill J. K, Butter C, Giovannoni G, Amor S, Baker D (2012a) Practical guide to the induction of relapsing progressive experimental autoimmune encephalomyelitis in the Biozzi ABH mouse. Mult Scler Rel Dis 1: 29-38

Al-Izki S, Pryce G, Hankey D J, Lidster K, von Kutzleben S M, Browne L, Clutterbuck L, Posada C, Edith Chan A W, Amor S et al (2014) Lesional-targeting of neuroprotection to the inflammatory penumbra in experimental multiple sclerosis. Brain: a journal of neurology 137: 92-108

Al-Izki S, Pryce G, O'Neill J K, Butter C, Giovannoni G, Amor S, Baker D (2012b) Practical guide to the induction of relapsing progressive experimental autoimmune encephalomyelitis in the Biozzi ABH mouse. Multiple Sclerosis and Related Disorders 1: 29-38

Amor S, Groome N, Linington C, Morris M M, Dornmair K, Gardinier M V, Matthieu J M, Baker D (1994) Identification of epitopes of myelin oligodendrocyte glycoprotein for the induction of experimental allergic encephalomyelitis in SJL and Biozzi AB/H mice. J Immunol 153: 4349-4356

Astin R, Bentham R, Djafarzadeh S, Horscroft J A, Kuc R E, Leung P S, Skipworth J R, Vicencio J M, Davenport A P, Murray A J et al (2013) No evidence for a local renin-angiotensin system in liver mitochondria. Scientific reports 3: 2467

Bainbridge J W, Stephens C, Parsley K, Demaison C, Halfyard A, Thrasher A J, Ali R R (2001) In vivo gene transfer to the mouse eye using an HIV-based lentiviral vector; efficient long-term transduction of corneal endothelium and retinal pigment epithelium. Gene therapy 8: 1665-1668.

Baker D, Gerritsen W, Rundle J, Amor S (2011) Critical appraisal of animal models of multiple sclerosis. Mult Scler 17: 647-657

Jackson S J, Pryce G, Diemel L T, Cuzner M L, Baker D (2005) Cannabinoid-receptor 1 null mice are susceptible to neurofilament damage and caspase 3 activation. Neuroscience 134: 261-268

Lim S Y, Hausenloy D J, Arjun S, Price A N, Davidson S M, Lythgoe M F, Yellon D M (2011) Mitochondrial cyclophilin-D as a potential therapeutic target for post-myocardial infarction heart failure. Journal of cellular and molecular medicine 15: 2443-2451

McEwan W A, Schaller T, Ylinen L M, Hosie M J, Towers G J, Willett B J (2009) Truncation of TRIM5 in the Feliformia explains the absence of retroviral restriction in cells of the domestic cat. Journal of virology 83: 8270-827

Naldini L, Blömer U, Gallay P, Ory D, Mulligan R, Gage F H, Verma I M, Trono D (1996) In vivo gene delivery and stable transduction of non-dividing cells by a lentiviral vector. Science 272: 263-26

Nikolovska et al, 2004, Development and optimization of a binding assay for the XIAP BIR3 domain using fluorescence polarization. *Anal Biochem.* 332(2):261-73.

O'Neill J K, Baker D, Davison A N, Maggon K K, Jaffee B D, Turk J L (1992) Therapy of chronic relapsing experimental allergic encephalomyelitis and the role of the blood-brain barrier: elucidation by the action of Brequinar sodium. Journal of neuroimmunology 38: 53-62

Roehrl et al, 2004. A General Framework for Development and Data Analysis of Competitive High-Throughput Screens for Small-Molecule Inhibitors of Protein-Protein Interactions by Fluorescence Polarization., *Biochemistry.*, 43(51): 16056-66.

Schinkel A H, Wagenaar E, van Deemter L, Mol C A, Borst P (1995) Absence of the mdr1a P-Glycoprotein in mice affects tissue distribution and pharmacokinetics of dexamethasone, digoxin, and cyclosporin A. The Journal of clinical investigation 96: 1698-1705

Ylinen L M, Price A J, Rasaiyaah J, Hue S, Rose N J, Marzetta F, James L C, Towers G J (2010) Conformational Adaptation of Asian Macaque TRIMCyp Directs Lineage Specific Antiviral Activity. PLoS pathogens 6: e1001062

Zufferey R, Nagy D, Mandel R J, Naldini L, Trono D (1997) Multiply attenuated lentiviral vector achieves efficient gene delivery in vivo. Nature Biotech 15: 871-875

The invention claimed is:

1. A cyclosporin conjugate which is a compound of formula (I) or a pharmaceutically acceptable salt thereof:

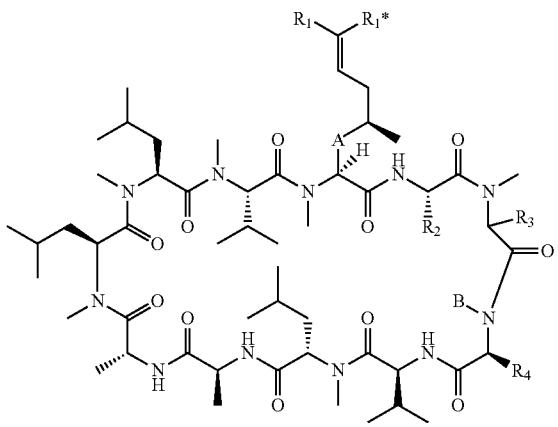

in which:

A represents

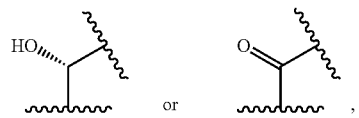

B represents methyl or ethyl, $R_2$ represents ethyl or isopropyl, $R_4$ represents —$CH_2CH(CH_3)CH_3$, —$CH_2CH(CH_3)CH_2CH_3$, —$CH(CH_3)CH_3$ or —$CH(CH_3)CH_2CH_3$, either (a) one of $R_1$ and $R_1^*$ represents -$L_1Z_1$ and the other represents hydrogen, and $R_3$ represents hydrogen, $C_1$-$C_3$ alkyl or $C_2$-$C_4$ alkenyl, (b) one of $R_1$ and $R_1^*$ represents methyl and the other represents hydrogen, and $R_3$ represents -$L_3Z_3$, or (c) one of $R_1$ and $R_1^*$ represents -$L_1Z_1$ and the other represents hydrogen, and $R_3$ represents -$L_3Z_3$, $L_1$ and $L_3$ independently represent a $C_1$-$C_6$ alkylene moiety, a $C_2$-$C_6$ alkenylene moiety or a —$(CH_2CH_2O)_n(CH_2)_m$— moiety in which n represents 1 to 3 and m represents 0 to 2, and $Z_1$ and $Z_3$ independently represent a moiety of formula (II*):

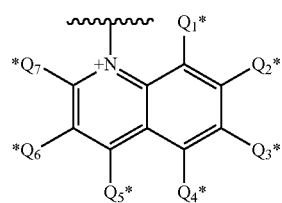

in which $Q_1^*$ to $Q_7^*$ independently represent a hydrogen atom, a $C_1$-$C_6$ haloalkyl group, a —OR' group, or a —NR'R" group, wherein R' and R" are the same or different and represent hydrogen or a $C_1$-$C_6$ alkyl group, and wherein four to seven of $Q_1^*$ to $Q_7^*$ represent hydrogen.

2. The conjugate according to claim 1, in which A represents

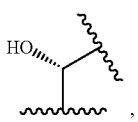

B represents methyl, R$_2$ represents ethyl and R$_4$ represents —CH$_2$CH(CH$_3$)CH$_3$.

3. The conjugate according to claim 1, in which R$_1$ represents -L$_1$Z$_1$, R$_1$* represents hydrogen and R$_3$ represents hydrogen, C$_1$-C$_3$ alkyl or C$_2$-C$_4$ alkenyl.

4. The conjugate according to claim 3, in which L$_1$ represents, a C$_1$-C$_6$ alkylene moiety.

5. The conjugate according to claim 1, in which R$_1$ represents methyl, R$_1$* represents hydrogen and R$_3$ represents -L$_3$Z$_3$.

6. The conjugate according to claim 5, in which L$_3$ represents a C$_2$-C$_6$ alkenylene moiety.

7. The conjugate according to claim 1, in which Z$_1$ and Z$_3$ independently represent a moiety of formula (II*a), (II*b) or (II*c):

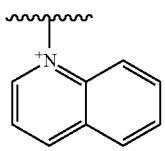
(II*a)

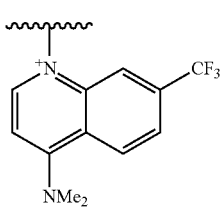
(II*b)

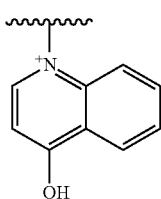
(II*c)

8. A pharmaceutical composition comprising a cyclosporin conjugate which is a compound of formula (I) or a pharmaceutically acceptable salt thereof:

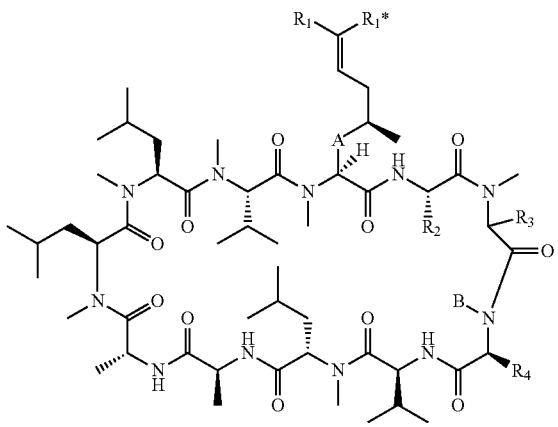
(I)

in which:
A represents

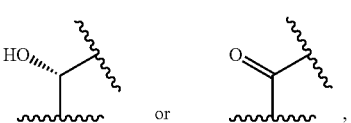

B represents methyl or ethyl,
R$_2$ represents ethyl or isopropyl,
R$_4$ represents —CH$_2$CH(CH$_3$)CH$_3$, —CH$_2$CH(CH$_3$)CH$_2$CH$_3$, —CH(CH$_3$)CH$_3$ or —CH(CH$_3$)CH$_2$CH$_3$,
either (a) one of R$_1$ and R$_1$* represents -L$_1$Z$_1$ and the other represents hydrogen, and R$_3$ represents hydrogen, C$_1$-C$_3$ alkyl or C$_2$-C$_4$ alkenyl, (b) one of R$_1$ and R$_1$* represents methyl and the other represents hydrogen, and R$_3$ represents -L$_3$Z$_3$, or (c) one of R$_1$ and R$_1$* represents -L$_1$Z$_1$ and the other represents hydrogen, and R$_3$ represents -L$_3$Z$_3$,
L$_1$ and L$_3$ independently represent a C$_1$-C$_6$ alkylene moiety, a C$_2$-C$_6$ alkenylene moiety or a —(CH$_2$CH$_2$O)$_n$(CH$_2$)$_m$— moiety in which n represents 1 to 3 and m represents 0 to 2, and
Z$_1$ and Z$_3$ independently represent a moiety of formula (II*):

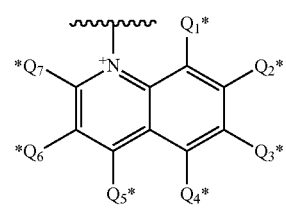
(II*)

in which Q$_1$* to Q$_7$* independently represent a hydrogen atom, a C$_1$-C$_6$ haloalkyl group, a —OR' group, or a —NR'R" group, wherein R' and R" are the same or different and represent hydrogen or a C$_1$-C$_6$ alkyl group, and wherein four to seven of Q$_1$* to Q$_7$* represent hydrogen,
and a pharmaceutically acceptable excipient, diluent or carrier.

9. A method of treating a patient suffering from or susceptible to disease or disorder susceptible to amelioration by inhibition of cyclophilin D, which method comprises administering to said patient a cyclosporin conjugate which is a compound of formula (I) or a pharmaceutically acceptable salt thereof:

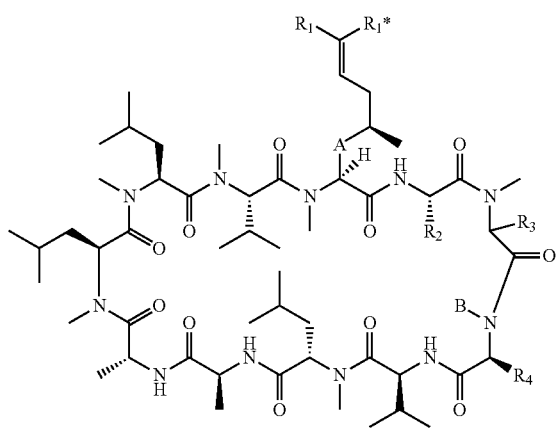

in which:
A represents

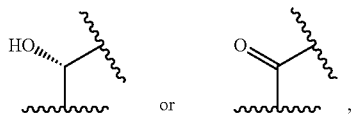

B represents methyl or ethyl, $R_2$ represents ethyl or isopropyl, $R_4$ represents —$CH_2CH(CH_3)CH_3$, —$CH_2CH(CH_3)CH_2CH_3$, —$CH(CH_3)CH_3$ or —$CH(CH_3)CH_2CH_3$, either (a) one or $R_1$ and $R_1^*$ represents -$L_1Z_1$ and the other represents hydrogen, and $R_3$ represents hydrogen, $C_1$-$C_3$ alkyl or $C_2$-$C_4$ alkenyl, or (b) one of $R_1$ and $R_1^*$ represents methyl and the other represents hydrogen, and $R_3$ represents -$L_3Z_3$, or (c) one or $R_1$ and $R_1^*$ represents -$L_1Z_1$ and the other represents hydrogen, and $R_3$ represents -$L_3Z_3$, $L_1$ and $L_3$ independently represent a $C_1$-$C_6$ alkylene moiety, a $C_2$-$C_6$ alkenylene moiety or a —$(CH_2CH_2O)_n(CH_2)_m$— moiety in which n represents 1 to 3 and m represents 0 to 2, and $Z_1$ and $Z_3$ independently represent a quinolium ring which is unsubstituted or substituted by one or more substituents selected from a halogen atom, a $C_1$-$C_6$ alkyl group, a $C_1$-$C_6$ haloalkyl group, a —OR' group, a —COOR' group, a —CONR'R" group and a —NR'R" group, wherein R' and R" are the same or different and represent hydrogen or a $C_1$-$C_6$ alkyl group.

10. The method according to claim 9, wherein said disease or disorder is ischaemia/reperfusion injury or neurodegenerative disease.

* * * * *